United States Patent [19]

Trinks et al.

[11] Patent Number: 5,663,336

[45] Date of Patent: Sep. 2, 1997

[54] SUBSTITUTED DIAMINOPHTHALIMIDES AND ANALOGUES

[75] Inventors: Uwe Trinks, Münchenstein; Peter Traxler, Schönenbuch, both of Switzerland

[73] Assignee: Ciba-Geigy Corporation, Tarrytown, N.Y.

[21] Appl. No.: 544,525

[22] Filed: Oct. 18, 1995

Related U.S. Application Data

[63] Continuation of Ser. No. 360,864, Dec. 21, 1994, Pat. No. 5,491,144, which is a continuation of Ser. No. 124,915, Sep. 21, 1993, abandoned, which is a continuation-in-part of Ser. No. 890,218, May 28, 1992, abandoned.

[30] Foreign Application Priority Data

May 30, 1991 [CH] Switzerland .................. 1601/91

[51] Int. Cl.$^6$ .................. C07D 401/04; C07D 403/04; C07D 209/48; C07D 241/38
[52] U.S. Cl. .................. 544/212; 544/296; 544/345; 546/256; 548/312.1; 548/467; 548/472; 548/473; 548/474; 548/475; 548/476
[58] Field of Search .................. 514/245, 250, 514/256, 275, 333, 397, 414, 416, 417; 546/256; 548/312.1, 467, 472, 473, 474, 475, 476; 544/212, 296, 345

[56] References Cited

U.S. PATENT DOCUMENTS

| | | | |
|---|---|---|---|
| 2,508,418 | 5/1950 | Strain et al. | 260/326 |
| 2,556,664 | 6/1951 | Smith et al. | 548/476 |
| 2,995,559 | 8/1961 | Ruschig et al. | 548/476 |
| 3,001,998 | 9/1961 | Ruschig et al. | 548/476 |
| 3,308,135 | 3/1967 | Jansen et al. | 260/326 |
| 3,644,405 | 2/1972 | Horstmann et al. | 548/475 |
| 3,857,947 | 12/1974 | Teach | 514/417 |
| 3,980,634 | 9/1976 | Weaver | 534/789 |
| 4,039,522 | 8/1977 | Weaver et al. | 534/789 |
| 4,363,917 | 12/1982 | Fischer et al. | 548/480 |

FOREIGN PATENT DOCUMENTS

| | | |
|---|---|---|
| 0516588 | 12/1992 | European Pat. Off. . |
| 1045244 | 10/1966 | United Kingdom . |
| 1484243 | 9/1977 | United Kingdom . |

OTHER PUBLICATIONS

House, C. et al., Europ. J. Biochem, 140, 363–367 (1984).
Akiyama, T. et al. Science 232, 1644 (1986).
Davis, et al. Tetrahedron Letters, 31, 5201–4 (1990).
Rosenmund et al., Ber. 52, 1749 (1916.
von Braun et al., Ann 488, 111 (1931).
The Merck Index, 10th edition, Merck & Co., Inc. Rahway, 1983, p. ONR–79.
Wöhrle, et al., Synthesis, Feb. 1993, pp. 194–196.
Matlin, et al. J. Chem Res. (M). 1920–1943 (1990).
Cronin et al., Cancer Research, vol. 46, pp. 4701–4705, (Sep. 1986).
Ozawa et al., Int. J. Cancer, vol. 40, pp. 706–710, (1987).
Weissman et al., Cell, vol. 32, pp. 599–606, (Feb. 1983).
Carpenter et al., Analytical Biochem., vol. 153, 279–282 (1985).
Meyer et al., Int J. Cancer, vol. 43, 851–856 (1989).
Matlin et al., J. Chem. Res., (1990) pp. 246–247.
White et al., J. Org. Chem. vol. 32, pp. 1921–1926.
Shephard. J. Chem. Soc. Perkins Trans. I 1495–1498 (1986.

Primary Examiner—Matthew V. Grumbling
Attorney, Agent, or Firm—Marla J. Mathias; Ronald J. Campbell

[57] ABSTRACT

A process for the synthesis of compounds of formula I

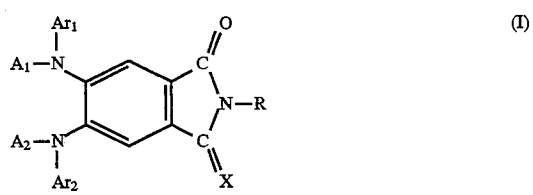

wherein $Ar_1$, $Ar_2$, $A_1$, $A_2$, R and X are as defined in the description, exhibit valuable pharmaceutical properties and are effective especially against diseases responsive to the inhibition of protein kinases, for example tumors.

3 Claims, No Drawings

SUBSTITUTED DIAMINOPHTHALIMIDES AND ANALOGUES

This is a Continuation of Ser. No. 08/360,864, filed Dec. 21st, 1994 now U.S. Pat. No. 5,991,194 which is a Continuation of Ser. No. 08/124,915, filed Sep. 21st, 1993 now abandoned which is a Continuation in-part of Ser. No. 07/890,218, filed May 28th, 1992 now abandoned.

The invention relates to compounds of formula I

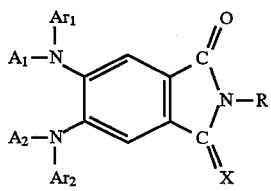

wherein $A_1$ and $A_2$ are each independently of the other hydrogen, lower alkyl, lower alkenyl, lower alkynyl, aryl, acyl, lower alkylsulfonyl or arylsulfonyl; or wherein $A_1$ and $A_2$ together form unsubstituted or lower alkyl- or hydroxy-substituted lower alkylene; $Ar_1$ and $Ar_2$ are each independently of the other aryl, heteroaryl or unsubstituted or substituted cycloalkyl; the group —C(=X)— is —C(=O)—, —C(=S)—, $CH_2$— or —C(=$CR_1R_2$)— wherein $R_1$ and $R_2$ are each independently of the other hydrogen or lower alkyl; and R is hydrogen, lower alkyl, aryl-lower alkyl, aryl, amine, hydroxy or lower alkoxy; with the proviso that R is other than phenyl when $A_1$ and $A_2$ are hydrogen, $Ar_1$ and $Ar_2$ are phenyl and the group —C(=X)— is —C(=O)—; and to salts thereof when salt-forming groups are present; to processes for the preparation of those compounds, to pharmaceutical compositions comprising those compounds, and to the use of those compounds for the therapeutic treatment of the human or animal body or for the preparation of pharmaceutical compositions.

The general terms used hereinbefore and hereinafter preferably have the following meanings within the scope of this Application:

The term "lower" denotes a radical having up to and including 7, especially up to and including 4, and more especially having 1 or 2, carbon atoms.

Lower alkyl is preferably n-propyl, isopropyl, n-butyl, isobutyl, sec-butyl, tert-butyl, n-pentyl, neopentyl, n-hexyl or n-heptyl, preferably ethyl and especially methyl.

Lower alkenyl has from 2 to 7, preferably from 2 to 4, carbon atoms and is, for example, allyl or crotyl.

Lower alkynyl has from 2 to 7, preferably from 2 to 4 carbon atoms and is, for example, propyn-1-yl or propyn-2-yl or 2-butyn-1-yl.

Lower alkyl substituted by halogen is, for example, trifluoromethyl.

Aryl is preferably phenyl or naphthyl, such as 1- or 2-naphthyl. The phenyl and naphthyl radicals can be unsubstituted or substituted, especially as indicated below for phenyl. Aryl is preferably phenyl that is unsubstituted or substituted by one or more, especially one to three, for example one or two, substituents selected independently from the group consisting of: hydrocarbyl, for example lower alkyl, lower alkenyl, lower alkynyl, lower alkylene (linked to two adjacent carbon atoms), cycloalkyl, phenyl-lower alkyl or phenyl; substituted hydrocarbyl, for example lower alkyl substituted, for example, by hydroxy, lower alkoxy, phenyl-lower alkoxy, lower alkanoyloxy, halogen, amine, lower alkyl-amino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; etherified hydroxy, for example lower alkoxy, halo-lower alkoxy, phenyl-lower alkoxy, phenoxy, lower alkenyloxy, halo-lower alkenyloxy, lower alkynyloxy or lower alkylenedioxy (linked to two adjacent carbon atoms); esterified hydroxy, for example lower alkanoyloxy, phenyl-lower alkanoyloxy or phenylcarbonyloxy (= benzoyloxy); mercapto; etherified mercapto, which is optionally oxidised, for example lower alkylthio, phenyl-lower alkylthio, phenylthio, lower alkylsulfinyl [—S(=O)-lower alkyl], phenyl-lower alkylsulfinyl, phenylsulfinyl, lower alkylsulfonyl [—S($O_2$)-lower alkyl], phenyl-lower alkylsulfonyl or phenylsulfonyl; halogen; nitro; amine; monohydrocarbylamino, for example lower alkylamino, cycloalkylamino, phenyl-lower alkylamino or phenylamino; dihydrocarbylamino, for example di-lower alkylamino, N-lower alkyl-N-phenylamino, N-lower alkyl-N-phenyl-lower alkylamino, lower alkyleneamino, or lower alkyleneamino interrupted by —O—, —S— or —NR" (wherein R" is hydrogen, alkyl or acyl); acylamino, for example lower alkanoylamino, phenyl-lower alkanoylamino or phenylcarbonylamino (= benzoylamino); acyl, for example lower alkanoyl, phenyl-lower alkanoyl or phenylcarbonyl (=benzoyl); carboxy; esterified carboxy, for example lower alkoxycarbonyl; amidated carboxy, for example carbamoyl, N-lower alkylcarbamoyl, N,N-di-lower alkylcarbamoyl, N-hydroxycarbamoyl or N-phenylcarbamoyl; cyano; sulfo ($SO_3H$); esterified sulfo, for example lower alkoxysulfonyl; and amidated sulfo, for example sulfamoyl ($SO_2NH_2$), N-lower alkylsulfamoyl, N,N-di-lower alkylsulfamoyl or N-phenylsulfamoyl; phenyl groups occurring in the substituents each being unsubstituted or substituted by lower alkyl, lower alkoxy, hydroxy, halogen and/or by trifluoromethyl.

R is preferably selected from all the above-mentioned definitions except aryl.

Heteroaryl is a heterocyclic radical of aromatic character and is preferably linked via a ring carbon atom. It is especially a 5- or 6-membered ring, for example imidazolyl, triazolyl, pyridyl, pyrimidinyl or triazinyl, and especially pyridyl. Those radicals may be unsubstituted or substituted, for example, by lower alkyl, hydroxy, lower alkoxy, halogen, cyano and/or by trifluoromethyl.

Pyridyl is, for example, 2-, 3- or 4-pyridyl.

Imidazolyl is, for example, 2- or 4(5)-imidazolyl.

Triazolyl is, for example, 1,2,4-triazol-3- or -4-yl or 1,2,3-triazol-4-yl.

Pyrimidinyl is, for example, 2-, 4- or 5-pyrimidinyl.

Triazinyl is, for example, 1,3,5-triazin-2-yl.

Lower alkylene, formed from $A_1$ and $A_2$ together, is unbranched and is especially a $(CH_2)_n$ group wherein n is from 1 to 4, preferably 2 or 3. It is preferably unsubstituted but may also be substituted by lower alkyl or hydroxy.

Lower alkylene, linked to two adjacent carbon atoms of a benzene ring, is preferably. $C_3$–$C_4$ alkylene, for example 1,3-propylene or 1,4-butylene.

Lower alkylenedioxy, linked to two adjacent carbon atoms, is preferably $C_{1-C2}$ alkylenedioxy, for example methylene- or 1,2-ethylene-dioxy.

Lower alkyleneamino is preferably $C_4$–$C_7$- and especially $C_4$–$C_5$-alkyleneamino, for example piperidino. Lower alkyleneamino interrupted by —O—, —S— or —NR"— is preferably $C_4$–$C_7$- and especially $C_4$–$C_5$-alkyleneamino in which a ring carbon atom has been replaced by the corresponding hetero group, and is especially morpholino, thiomorpholino, piperazino or 4-lower alkyl- or 4-lower alkanoyl-piperazino.

Acyl is preferably lower alkanoyl, halo-lower alkanoyl, aryl-lower alkanoyl or aryl carbonyl. Acyl is especially lower alkanoyl.

Lower alkanoyl is preferably formyl, acetyl, propionyl, n-butyryl, pivaloyl or valeroyl, especially acetyl.

Aryl-lower alkyl is preferably phenyl-lower alkyl and especially benzyl.

Cycloalkyl is preferably $C_3$–$C_8$- and especially $C_5$–$C_7$-cycloalkyl, which is intended to indicate that it contains from 3 to 8 and from 5 to 7 ring carbon atoms, respectively. It may, however, also be substituted, for example by lower alkyl or hydroxy.

Halogen is especially fluorine, chlorine and bromine, but may also be iodine.

Salts of compounds according to the invention having salt-forming groups are especially pharmaceutically acceptable, non-toxic salts. For example, compounds of formula I having basic groups may form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or with amino acids, such as arginine or lysine. Compounds of formula I having an acidic group, for example carboxy, form, for example, metal or ammonium salts, such as alkali metal and alkaline earth metal salts, for example sodium, potassium, magnesium or calcium salts, and also ammonium salts with ammonia or suitable organic amines, such as lower alkylamines, for example triethylamine, hydroxy-lower alkylamines, for example 2-hydroxyethylamine, bis(2-hydroxyethyl)amine or tris(2-hydroxyethyl)amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylene-diamine, dibenzylamine or benzyl-B-phenethylamine. Compounds of formula I having an acidic group and a basic group can also be in the form of internal salts, that is to say in zwitterionic form.

The salts of compounds according to the invention also include complexes of compounds of formula I ($A_1$, $A_2$=hydrogen) with transition metal ions, for example copper, cobalt or manganese.

For the purposes of isolation or purification it is also possible to use pharmaceutically unacceptable salts, for example picrates or perchlorates. Only the pharmaceutically acceptable, non-toxic salts are used therapeutically and these are therefore preferred.

The compounds according to the invention have valuable, especially pharmacologically acceptable, properties. In particular they exhibit specific inhibitory activities that are of pharmacological interest. They act especially as tyrosine protein kinase inhibitors and exhibit, for example, a potent inhibition of the tyrosine kinase activity of the receptor for the epidermal growth factor (EGF) and the c-erbB2 kinase. These receptor-specific enzyme activities play a key role in the signal transmission in a large number of mammal cells, including human cells, especially epithelial cells, cells of the immune system and cells of the central and peripheral nervous system. The EGF-induced activation of the receptor-associated tyrosine protein kinase (EGF-R-PTK) is in various cell types a prerequisite for cell division and thus for the proliferation of a cell population. The addition of EGF-receptor-specific tyrosine kinase inhibitors therefore inhibits the reproduction of those cells.

The inhibition of EGF-receptor-specific tyrosine protein kinase (EGF-R-PTK) can be demonstrated for example, using the method of C. House et al., Europ. J. Biochem. 140, 363–367 (1984). The compounds according to the invention preferentially inhibit the enzyme activity by 50% ($IC_{50}$) in 0.1–10 μM concentration. Furthermore, in the micromolar range too, for example, they also exhibit an inhibition of the cell growth of an EGF-dependent cell line, for example the epidermoid mouse keratinocyte cell line. In order to measure this inhibition of cell growth, the EGF-stimulated cell proliferation of epidermal BALB/MK keratinocytes is used (description of the method in Meyer, T., et al., Int. J. Cancer 43, 851 (1989)). Those cells are to a high degree dependent upon the presence of EGF for proliferation (Weissmann, B. E., Aaronson, S. A., Cell 32, 599 (1983)). In order to carry out the test, BALB/MK cells (10 000/well) are transferred to 96-well microtiter plates and incubated overnight. The test substances (dissolved in DMSO) are added in various concentrations (in dilution series) so that the final concentration of DMSO is no greater than 1%. After the addition, the plates are incubated for three days, during which time the control cultures without the test substance are able to undergo at least three cell division cycles. The growth of the MK cells is measured by means of methylene blue staining. The $IC_{50}$ value is defined as that concentration of the test substance in question which results in a 50% decrease in comparison with the control cultures without inhibitor. When BALB/MK cells are transplanted into BALB/c nu/nu mice (Bomholtgard, Denmark), the growth of the resulting tumors can be suppressed in vivo by oral administration of a compound of the present invention.

In addition to inhibiting EGF-R-PTK, the compounds according to the invention also inhibit other tyrosine kinases that are involved in signal transmission mediated by trophic factors, for example the abl-kinase, kinases from the family of src-kinases and the c-erbB2 kinase (HER-2), and also serine/threonine kinases, for example protein kinase C, all of which have a role to play in growth regulation and transformation in the cells of mammals, including humans.

The inhibition of the c-erbB2 tyrosine kinase (HER-2) can be demonstrated, for example, analogously to the method of C. House et al., Europ. J. Biochem. 140, 363–367 (1984) used for EGF-R-PTK. The c-erbB2 kinase can be isolated, and its activity determined, in accordance with known protocols, for example in accordance with T. Akiyama et at., Science 232, 1644 (1986).

The compounds according to the invention are therefore also suitable for the inhibition of processes mediated by these and related tyrosine kinases.

The compounds according to the invention are therefore useful, for example, in the treatment of benign or malignant tumours. They are able to bring about the regression of tumours and to prevent the formation of tumour metastases and the growth of micrometastases. In particular, they can be used in epidermal hyperproliferation (psoriasis), in the treatment of neoplasias of epithelial character, for example mammary carcinoma, and in leukaemias. In addition, the compounds can be used in the treatment of diseases of the immune system and in the treatment of inflammation insofar as protein kinases are involved in those disorders. The compounds can also be used in the treatment of disorders of the central or peripheral nervous system insofar as signal transmission by protein kinases is involved.

The compounds according to the invention can be used both on their own and in combination with other pharmacologically active substances, for example together with (a) inhibitors of enzymes of polyamine synthesis, (b) inhibitors of protein kinase C, (c) inhibitors of other tyrosine kinases, (d) cytokines, (e) negative growth regulators, for example TGF-β or IFN-β, (f) aromatase inhibitors, (g) anti-oestrogens or (h) cytostatics.

The invention relates especially to compounds of formula I wherein $A_1$ and $A_2$ are each independently of the other hydrogen, lower alkyl, aryl, acyl, lower alkylsulfonyl or arylsulfonyl; or wherein $A_1$ and $A_2$ together are unsubstituted or lower alkyl- or hydroxy-substituted lower alkylene; $Ar_1$ and $Ar_2$ are each independently of the other aryl, heteroaryl or unsubstituted or substituted cycloalkyl; the group —C(=X)— is —C(=O)—, —C(=S)—, —CH$_2$— or —C(=CR$_1$R$_2$)— wherein $R_1$ and $R_2$ are each independently of the other hydrogen or lower alkyl; and R is hydrogen, lower alkyl, aryl-lower alkyl, alkyl, amine, hydroxy or lower alkoxy; with the proviso that R is other than phenyl when $A_1$ and $A_2$ are hydrogen, $Ar_1$ and $Ar_2$ are phenyl and the group —C(=X)— is —C(=O)—, and salts thereof when salt-forming groups are present.

The invention preferably relates to compounds of formula I wherein $A_1$ and $A_2$ are each independently of the other hydrogen, lower alkyl; lower alkenyl; phenyl or 1-naphthyl or 2-naphthyl, the three last-mentioned radicals being unsubstituted or substituted by lower alkyl, lower alkoxy, hydroxy, halogen and/or by trifluoroethyl; lower alkanoyl, lower alkylsulfonyl or phenylsulfonyl wherein the phenyl group is unsubstituted or substituted by lower alkyl, lower alkoxy, hydroxy, halogen and/or by trifluoromethyl; or wherein $A_1$ and $A_2$ together are $C_1$–$C_4$alkylene; wherein $Ar_1$ and $Ar_2$ are each independently of the other phenyl or naphthyl, each of which is unsubstituted or substituted by one or more substituents from the group consisting of: lower alkyl, lower alkenyl, lower alkynyl, lower alkylene (linked to two adjacent carbon atoms), $C_3$–$C_8$cycloalkyl, phenyl-lower alkyl, phenyl; lower alkyl substituted by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy, lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenylalkylsulfonyl, phenylsulfonyl, halogen, nitro, amino, lower alkylamino, $C_3$–$C_8$cycloalkylamino, phenyl-lower alkylamino, phenylamino, all-lower alkylamino, N-lower alkyl-N-phenylamino, N-lower alkyl-N-phenyl-lower alkylamino, lower alkyleneamino, lower alkyleneamino interrupted by —O—, —S— or —NR" (wherein R" is hydrogen, lower alkyl or lower alkanoyl), lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N-hydroxycarbamoyl, N-phenylcarbamoyl, cyano, sulfo, lower alkylsulfonyl, sulfamoyl, N-lower alkylsulfamoyl, N,N-di-lower alkylsulfamoyl and N-phenylsulfamoyl (phenyl groups occurring in the substituents each being unsubstituted or substituted by lower alkyl, lower alkoxy, hydroxy, halogen and/or by trifluoromethyl); pyridyl or pyrimidinyl that is unsubstituted or substituted by lower alkyl, hydroxy, lower alkoxy, halogen, cyano and/or by trifluoromethyl; or $C_3$–$C_8$cycloalkyl; the group —C(=X)— is —C(=O)—, —C(=S)—, —CH$_2$— or —C(=CR$_1$R$_2$)— wherein $R_1$ and $R_2$ are each independently of the other hydrogen or lower alkyl, and R is hydrogen, lower alkyl, phenyl-lower alkyl, phenyl, 1-naphthyl or 2-naphthyl, in the four last-mentioned radicals the phenyl or naphthyl group being unsubstituted or substituted by lower alkyl, lower alkoxy, hydroxy, halogen and/or by trifluoromethyl; or R is amino, hydroxy or lower alkoxy, with the proviso that R is other than phenyl when $A_1$ and $A_2$ are hydrogen, $Ar_1$ and $Ar_2$ are phenyl and the group —C(=X)— is —C(=O)—; and salts thereof when salt-forming groups are present.

Of those last-mentioned compounds of formula I, very special preference is given to those wherein R is as defined except for phenyl, and the other radicals are as defined, and salts thereof when salt-forming groups are present.

The invention relates more especially to compounds of formula I wherein $A_1$ and $A_2$ are each independently of the other hydrogen, lower alkyl; phenyl or 1-naphthyl or 2-naphthyl, the three last-mentioned radicals being unsubstituted or substituted by lower alkyl, lower alkoxy, hydroxy, halogen and/or by trifluoromethyl; lower alkanoyl, lower alkylsulfonyl or phenylsulfonyl wherein the phenyl group is unsubstituted or substituted by lower alkyl, lower alkoxy, hydroxy, halogen and/or by trifluoromethyl; or wherein $A_1$ and $A_2$ together are $C_1$–$C_4$alkylene; wherein $Ar_1$ and $Ar_2$ are each independently of the other phenyl or naphthyl, each of which is unsubstituted or substituted by one or more substituents from the group consisting of: lower alkyl, lower alkenyl, lower alkynyl, lower alkylene (linked to two adjacent carbon atoms), $C_3$–$C_8$cycloalkyl, phenyl-lower alkyl, phenyl; lower alkyl substituted by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy, lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenylalkylsulfonyl, phenylsulfonyl, halogen, nitro, amino, lower alkylamino, $C_3$–$C_8$cycloalkylamino, phenyl-lower alkylamino, phenylamino, di-lower alkylamino, N-lower alkyl-N-phenylamino, N-lower alkyl-N-phenyl-lower alkylamino, lower alkyleneamino, lower alkyleneamino interrupted by —O—, —S— or —NR" (wherein R" is hydrogen, lower alkyl or lower alkanoyl), lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N-hydroxycarbamoyl, N-phenylcarbamoyl, cyano, sulfo, lower alkylsulfonyl, sulfamoyl, N-lower alkylsulfamoyl, N,N-di-lower alkylsulfamoyl and N-phenylsulfamoyl (phenyl groups occurring in the substitutes each being unsubstituted or substituted by lower alkyl, lower alkoxy, hydroxy, halogen and/or by trifluoromethyl); pyridyl that is unsubstituted or substituted by lower alkyl, hydroxy, lower alkoxy, halogen, cyano and/or by trifluoromethyl; or $C_3$–$C_8$cycloalkyl; the group —C(=X)— is —C(=O)—, —C(=S)—, —CH$_2$— or —C(=CR$_1$R$_2$)— wherein $R_1$ and $R_2$ are each independently of the other hydrogen or lower alkyl, and R is hydrogen, lower alkyl; phenyl-lower alkyl, phenyl, 1-naphthyl or 2-naphthyl, in the four last-mentioned radicals the phenyl or naphthyl group being unsubstituted or substituted by lower alkyl, lower alkoxy, hydroxy, halogen and/or by trifluoromethyl; or R is amino, hydroxy or lower alkoxy, with the proviso that R is other than phenyl when $A_1$ and $A_2$ are hydrogen, $Ar_1$ and $Ar_2$ are phenyl and the group —C(=X)— is —C(=O)—; and salts thereof when salt-forming groups are present.

The invention relates especially preferably to the compounds of formula I mentioned in the preceding paragraph wherein $A_1$ and $A_2$ are each independently of the other hydrogen or lower alkyl, the group —C(=X)— is —C(=O)—, —C(=S)— or —C(=CH$_2$)—, and R is hydrogen or lower alkyl, and salts thereof.

The invention relates more especially to compounds of formula I wherein $A_1$ and $A_2$ are each independently of the other hydrogen; lower alkyl; lower alkenyl; or lower alkanoyl; or wherein $A_1$ and $A_2$ together are $C_1$–$C_4$alkylene; wherein $Ar_1$ and $Ar_2$ are each independently of the other phenyl or naphthyl, each of which is unsubstituted or substituted by one or more substituents from the group consisting of: lower alkyl, lower alkylene (linked to two adjacent carbon atoms), hydroxy, phenoxy, halogen, nitro, amino, lower alkylamino, di-lower alkylamino, lower alkanoylamino, carboxy, lower alkoxycarbonyl, carbamoyl, N-lower alkylcarbamoyl, N,N-di-lower alkylcarbamoyl and cyano, or in addition from lower alkoxy; pyridyl; pyrimidinyl; or $C_3$–$C_8$cycloalkyl; the group —C(=X)— is —C(=O)— or —C(=S)—, and R is hydrogen, lower alkyl, phenyl-lower alkyl, amino or hydroxy; and salts thereof when salt-forming groups are present.

The invention relates even more especially to compounds of formula I wherein $A_x$ and $A_2$ are each independently of the other hydrogen or methyl; or wherein $A_1$ and $A_2$ together are —(CH$_2$)$_2$— or —(CH$_2$)$_3$—; $Ar_1$ and $Ar_2$ are each independently of the other phenyl or naphthyl, each of which is unsubstituted or substituted by one or more substituents from the group consisting of: lower alkyl, lower alkoxy, phenyl-lower alkoxy, hydroxy, lower alkanoyloxy, nitro, amino, lower alkylamino, all-lower alkylamino, lower alkanoylamino, halogen, trifluoromethyl, carboxy, lower alkoxycarbonyl, carbamoyl, N-lower alkylcarbamoyl, N,N-di-lower alkylcarbamoyl, cyano, lower alkanoyl, benzoyl, lower alkylsulfonyl and sulfamoyl, N-lower alkylsulfamoyl and N,N-di-lower alkylsulfamoyl; cyclopentyl; cyclohexyl; or pyridyl; the group —C(=X)— is —C(=O)—, —C(=S)— or —C(=CH$_2$)—, and R is hydrogen or lower alkyl; and pharmaceutically acceptable salts thereof.

The invention relates most especially to compounds of formula I wherein $A_1$ and $A_2$ are hydrogen; $Ar_1$ and $Ar_2$ are each independently of the other phenyl that is unsubstituted or substituted by lower alkyl, trifluoromethyl, phenyl, hydroxy, lower alkoxy, benzyloxy, amino, di-lower alkylamino, lower alkanoylamino, halogen, carboxy, lower alkoxycarbonyl, carbamoyl, N,N-di-lower alkylcarbamoyl or by cyano; or cyclohexyl; the group —C(=X)— is —C(=O)—, —C(=S)— or —C(=CH$_2$)—, and R is hydrogen; and pharmaceutically acceptable salts thereof.

The invention relates more especially to the specific compounds described in the Examples and pharmaceutically acceptable salts thereof.

The compounds of formula I can be prepared, for example by (a) reacting a compound of formula II

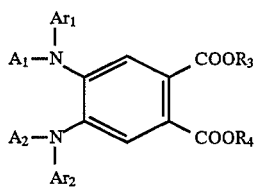

(II)

wherein $Ar_1$, $Ar_2$, $A_1$ and $A_2$ are as defined under formula I and $R_3$ and $R_4$ are each independently of the other hydrogen, aryl or lower alkyl, with a compound of formula III $H_2N$—R   (III)

wherein R is as defined under formula I or with urea, when each if $R_3$ and $R_4$ is hydrogen, or (b) reacting a compound of formula IV

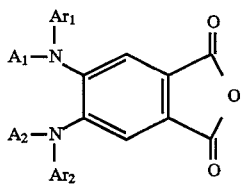

(IV)

wherein Ar and A are as defined under formula I, with a compound of formula III $H_2N$—R   (III)

wherein R is as defined under formula I, or with formamide and an ensuing hydrolysis;

and, if desired, or converting a resulting compound of formula I into a different compound of formula I, and/or converting a resulting salt into the free compound or into a different salt, and/or converting a resulting free compound I into a salt and/or separating a resulting mixture of isomeric compounds of formula I into the individual isomers.

In the following, more detailed description of the processes, the symbols $Ar_1$, $Ar_2$, $A_1$, $A_2$, X, R, $R_3$ and $R_4$ are each as defined under formulae I and II unless indicated to the contrary.

Process (a)

The reaction according to process (a) corresponds to the aminolysis, known per se, of phthalic acid diesters with ammonia or primary amines. The reaction with activated phthalic acid diesters, for example the di(p-nitrophenyl) ester, normally takes place at room temperature, but the reaction with di-lower alkyl esters generally takes place only at high temperatures. Preferably either the free acid or the dimethyl ester is used. Preferred is the reaction of di-lower alkyl esters in a solvent, especially in a high-boiling alcohol, for example a diol, such as ethylene glycol or 2-ethoxyethanol, at temperatures of from 100° to 150° C., for example approximately 120° C., or the reaction of the lower alkyl esters with ammonia or the respective amine of formula II is carried out at the same temperatures in the presence of a solvent, for example an alcohol, such as a lower alkanol, for example methanol or ethanol, or in the absence of a solvent, in an autoclave at elevated pressure. When $R_3$ and $R_4$ are hydrogen, reaction with urea instead of the compound of formula III is preferred, and the reaction preferably takes place in an aromatic hydrocarbon, such as toluene or xylene, in the presence of excess urea.

The starting compounds of formula II are prepared, for example, by reacting a cyclohexadiene of formula V

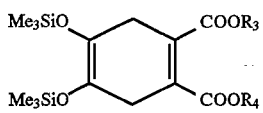
(V)

wherein Me is methyl, with an aniline of formula VI

  AHN—Ar (VI)

wherein A is especially hydrogen or lower alkyl, under acid catalysis [see Matlin, Stephen A. and Barron, Kenneth, J. Chem. Res. Synop. 8, 246–247 (1990)].

The preparation of the compounds of formula V is effected, for example, by means of a Diels-Alder reaction and is likewise described in the literature mentioned.

For the preparation of asymmetrical compounds of formula II, wherein $A_1$ and $A_2$ and/or $Ar_1$ and $Ar_2$ are different, for example compounds of formula V can be reacted—for example stepwise—with two different compounds of formula VI and the desired compounds of formula II can be isolated by chromatographic separation.

Furthermore, for example, compounds of formula II wherein $A_1=A_2H$ can be reacted in a ratio of 1:1 with a lower alkyl-introducing agent, for example methyl iodide, yielding asymmetrical compounds of formula II wherein $A_1$=lower alkyl and $A_2$=H. If the lower alkyl-introducing agent is used in excess, for example 10:1, then symmetrical compounds of formula II wherein $A_1=A_2$=lower alkyl are obtained.

Where necessary, in a compound of formula III, wherein R is amino or hydroxy, R may also be present in benzyloxycarbonyl protected form. Removal of the protecting group is effected according to murine methods, for example by hydrogenation in the presence of a catalyst, such as Pd on charcoal in an alcoholic solution, such as ethanol.

Process (b)

The reaction according to process (b) corresponds to the aminolysis, known per se of phthalic acid anhydrides, for example with ammonia or primary amines at relatively high temperatures, for example in 2-ethoxyethanol, tetrahydrofurane (in the latter solvent preferably with simultaneous evaporation of the solvent) or with hexamethyldisilazane and methanol at room temperature [Davis, Peter D. and Bit, Rino A., Tetrahedron Lett. 31, 5201–5204 (1990)].

When instead of the compound of formula III formamide is used, the reaction is carried out preferably without solvent at about 100° to about 130° C., followed by hydrolysis with water, for example at about 30° to about 80° C. (of. Synthesis 1993, 194–195).

The starting compounds of formula IV are prepared, for example, by reacting a compound of formula VII

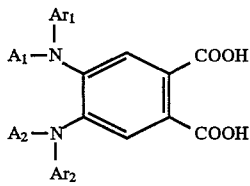
(VII)

with an acid anhydride of formula VIII, $(R_5CO)(R_5'CO)O$, wherein $R_5$ and $R_5'$ are each independently of the other hydrogen or lower alkyl, but are not both hydrogen.

The compounds of formula VII can be obtained, for example, by hydrolysis, for example in an acidic or alkaline medium (such as an alkali metal hydroxide, preferably lithium or sodium hydroxide, in an alcohol, preferably methanol or ethanol, in the presence of water), of a corresponding compound of formula II.

Compounds of formula I can be converted into different compounds of formula I.

For example, a compound of formula I wherein the group —C(=X)— is —C(=O)— can be reacted with a suitable reagent in order to obtain a different compound of formula I wherein the group —C(=X)— is —C(=S)—, —CH$_2$— or —C(=CR$_1$R$_2$)—. A suitable reagent for the conversion of —C(=O)— into —C(=S)— is, for example, the Lawesson reagent (=2,4-bis(4-methoxyphenyl)-2,4-dithioxo-1,3,2, 4-dithiaphosphetane), the reaction being carried out, for example, in a halogenated hydrocarbon, such as dichloromethane, or in toluene, at temperatures of from 30° C. to the reflux temperature, especially at reflux temperature or 100° C. Suitable systems for the conversion of —C(=O)— into —CH$_2$— are, for example, LiAlH$_4$/ tetrahydrofuran, zinc amalgam/HCl/ethanol or Raney-Nickel/H$_2$ in alcoholic solution, such as ethanol. The conversion of —C(=O)— into —C(=CR$_1$R$_2$)— is effected, for example, by reaction with a strong base, for example LDA (lithium diisopropylamide) and then with a Grignard reagent of the formula HCR$_1$R$_2$MgHal (Hal=halogen, for example iodine).

Furthermore, for example, compounds of formula I wherein R is hydrogen can be convened by alkylation, for example with lower alkyl or aryl-lower alkyl halides, after treatment with suitable bases, for example sodium hydride or potassium tert-butoxide, into different compounds of formula I wherein R is lower alkyl or aryl-lower alkyl.

Moreover, for example, compounds of formula I wherein $A_1$ and/or $A_2$ are hydrogen can be converted by reaction with suitable reagents into different compounds of formula I wherein $A_1$ and/or $A_2$ are lower alkyl, aryl, acyl, lower alkylsulfonyl or arylsulfonyl.

A suitable method for the introduction of $A_1$ and/or $A_2$=lower alkyl is, for example, treatment with the base LDA and subsequent reaction with a di-lower alkyl ether or a lower alkyl halide. Under those conditions a group —N(—R)—=—NH— which may be present in the molecule is alkylated only slightly or not at all.

For the introduction of $A_1$ and/or $A_2$=acyl, lower alkylsulfonyl or arylsulfonyl, the starting compound can be reacted, for example, again first with LDA and then with an acylating agent, for example acetyl chloride, or with an agent that introduces the lower alkylsulfonyl or arylsulfonyl group, for example methylsulfonyl chloride or p-toluenesulfonyl chloride.

Compounds of formula I wherein $Ar_1$ and/or $Ar_2$ are aryl, especially phenyl or naphthyl, substituted by halogen, preferably by bromine, can be converted into the corresponding derivatives in which one or all of the halogen atoms present in aryl $Ar_1$ and/or $Ar_2$ have been replaced by cyano, for example by reaction with a cyanide salt of a transition metal, especially CuCN, at temperatures of from 50° to 150° C., preferably from 60° to 140° C., in an inert polar solvent, such as an N,N-di-lower alkyl-lower alkanecarboxylic acid amide, for example dimethylformamide, with or without the subsequent addition of a catalyst, for example a transition metal halide, such as iron (III) chloride, in aqueous solution (see also Rosenmund et at., Ber. 52, 1749 (1916); von Braun et al., Ann. 488, 111 (1931)).

In compounds of formula I, the radicals $Ar_1$ and/or $Ar_2$ that are unsubstituted or substituted aryl, preferably unsubstituted phenyl or naphthyl, can be nitrated independently of one another, with the introduction of one or more nitro groups, for example under conditions customary for the introduction of a nitro group into aromatic compounds, for example with concentrated or 100% nitric acid at temperatures of from 0° to 100° C., preferably from 10° to 40° C., in an inert solvent, for example an organic acid anhydride, such as acetic anhydride. If the nitration results in several different products in which the number of nitro groups and their position(s) are different, they can be separated according to customary methods, for example by column chromatography.

Nitro substituents in radicals $Ar_1$ and/or $Ar_2$ can be reduced to amino groups, for example by hydrogenation under customary conditions, for example hydrogenation in the presence of a hydrogenation catalyst suitable for the selective reduction of nitro groups, such as Raney nickel, in an inert solvent, for example a cyclic or acyclic ether, such as tetrahydrofuran, under normal pressure or under elevated pressure of up to 5 bar.

Compounds of the formula I with etherified hydroxy groups, for example, with lower alkoxy residues as substituents within $Ar_1$ and/or $Ar_2$, can be convened into the corresponding hydroxy-substituted compounds of the formula I by ether cleavage. The ether cleavage takes place under conditions known per se, for example in the presence of hydrohalic adds, such as hydrobromic or hydroiodic, in the presence or absence of solvents, such as carbonic acids, for example, lower alkyl-carboni adds, such as acetic acid, at temperatures between 20° C. and the reflux temperature of the reaction mixture, or preferentially under mild conditions with boron halides, especially boron tribromide, in an inert solvent, for example a halogenated hydrocarbon, such as methylen chloride or chloroform, at temperatures between −80° and 0° C., preferably between −50° and 20° C.

Free compounds of formula I obtainable in accordance with the process having salt-forming properties can be converted into their salts in a manner known per se; compounds having basic properties can be converted into their salts, for example, by treatment with acids or suitable derivatives thereof, and compounds having acidic properties can be, converted into their salts, for example, by treatment with bases or suitable derivatives thereof.

Mixtures isomers obtainable in accordance with the invention can be separated into the individual isomers in a manner known per se; racemates can be separated, for example, by the formation of salts with optically pure salt-forming reagents and separation of the diastereoisomeric mixture so obtainable, for example by fractional crystallisation.

The above-mentioned reactions can be carried out under reaction conditions known per se, in the absence or; usually, in the presence of solvents or diluents, preferably those solvents or diluents which are inert towards the reagents used and are solvents therefor, in the absence or presence of catalysts, condensation agents or neutralising agents, and, depending upon the nature of the reaction and/or the reactants, at reduced, normal or elevated temperature, for example in a temperature range of from approximately −80° C. to approximately 200° C., preferably from approximately −20° C. to approximately 150° C., for example at the boiling point of the solvent used, under atmospheric pressure or in a closed vessel, where appropriate under pressure, and/or in an inert atmosphere, for example under a nitrogen atmosphere, and/or in the presence of antioxidants, such as ascorbic acid.

As a result of the close relationship between the compounds of formula I in free form and in the form of their salts, hereinbefore and hereinafter any reference to the free compounds or their salts should be understood as meaning also the corresponding salts or free compounds, respectively, when the compounds contain salt-forming groups, for example basic groups, such as amino or imino groups, and also those groups which contain no more than one unsaturated carbon atom, such as the groups —$NA_1Ar_1$ and/or —$NA_2Ar_2$ at the carbon atom of the central phenyl ring, wherein $Ar_1$ and $A_1$ and/or $Ar_2$ and $A_2$ are not bonded via an unsaturated carbon atom, and/or acidic groups, such as carboxy or sulfo ($SO_3H$).

The compounds, including their salts, can also be obtained in the form of hydrates, or their crystals may include, for example, the solvent used for crystallisation.

In the processes of this invention it is preferable to use those starting materials which result in the compounds described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

The present invention relates also to pharmaceutical compositions that comprise one of the compounds of formula I as active ingredient. Compositions for enteral, especially oral, and for parenteral administration are especially preferred. The compositions comprise the active ingredient on its own or, preferably, together with a pharmaceutically acceptable carrier. The dosage of the active ingredient depends upon the disease to be treated and upon the species, its age, weight and individual condition, and also upon the made of administration.

Preferred is a pharmaceutical composition suitable for administration to a warm-blooded animal, especially a human, suffering from a disease responsive to the inhibition of a protein kinase, for example psoriasis or a tumour, comprising a compound of formula I, or a salt thereof when salt-forming groups are present, in an amount effective for the inhibition of the protein kinase, together with at least one pharmaceutically acceptable carrier.

The pharmaceutical compositions comprise from approximately 5% to approximately 95% active ingredient, dosage forms in single dose form preferably comprising from approximately 20% to approximately 90% active ingredient and dosage forms that are not in single dose form preferably comprising from approximately 5% to approximately 20% active ingredient Unit dose forms, such as dragées, tablets or capsules, comprise from approximately 0.05 g to approximately 1.0 g of active ingredient.

The pharmaceutical compositions of this invention are prepared for example by means of conventional mixing, granulating, confectioning, dissolving or lyophilising processes. For example, pharmaceutical compositions for oral use can be obtained by combining the active ingredient with one or more solid carriers, optionally granulating a resulting mixture, and, if desired, processing the mixture or granules, if appropriate with the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders; such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil, liquid polyethylene glycols or fatty acid esters of ethylene or propylene glycol, to which stabiliser and detergents, for example of the polyoxethylen-sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration them are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, can also be in the form of a lyophilisate and can be made into a solution prior to parenteral administration by the addition of suitable solvents.

Solutions such as are used, for example, for parenteral administration can also be used as infusion solutions.

The invention relates also to a method of treating the above-mentioned pathological conditions, especially those conditions responsive to the inhibition of protein kinases. The compounds of this invention can be administered prophylactically or therapeutically, preferably in an mount effective against the said diseases, to a warm-blooded animal, for example a human, requiring such treatment, the compounds preferably being used in the form of pharmaceutical compositions. In the case of an individual having a body weight of about 70 kg the daily dose administered is from approximately 0.1 g to approximately 5 g, preferably from approximately 0.5 g to approximately 2 g, of a compound of this invention.

The following Examples illustrate the present invention; temperatures are given in degrees Celsius. The following abbreviations are used: ether =diethyl ether; THF= tetrahydrofuran; decomp.=under decomposition; DMF=N, N-dimethylformamide; h=hour(s); hexane=isomeric mixture of hexanes; min=minute(s); m.p.=melting point; MS =mass spectrum; FAB-MS=Fast Atom Bombardment Mass Spectroscopy; [M$^+$+H]=mass of molecule plus proton obtained by FAB-MS; FD-MS=Field Desorption MAss Spectroscopy; TLC=Thin Layer Chromatography; R$_f$=Ratio of fronts, when TLC data are given; RT=room temperature. Temperatures are given in Celsius degrees (° C.).

EXAMPLE 1

4,5-Bis(anilino)phthalimide

A suspension of 230 mg (0.7 mmol) of 4,5-bis(anilino) phthalic acid dimethyl ester in 23 ml of ethylene glycol is heated at 120°; ammonia gas is passed through the suspension, with stirring, for 24 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with dichloromethane/methanol 40:1 and the product fractions are combined and concentrated by evaporation, yielding the title compound in the form of yellow crystals, m.p. 215°–217°, FAB-MS: 330 [M$^+$+H].

a) 4,5-Bis(trimethylsilyloxy)cyclohexa-1,4-diene-1,2-dicarboxylic acid dimethyl ester Under argon, a solution of 7.1 g (50 mmol) of acetylenedicarboxylic acid dimethyl ester in 30 ml of toluene is added dropwise to 12.5 g (50 mmol) of 2,3-bis(trimethylsilyloxy) -1,3-butadiene (95%) and then boiled under reflux for 19 hours. The reaction mixture is cooled, the solvent is evaporated off and the residue is distilled under a high vacuum (0.1 mbar, 124°–127°), yielding the title compound in the form of a yellow, highly viscous oil, $^1$H-NMR (CDCl$_3$): δ=0.18 (s, 18H), 3.09 (s, 4H), 3.78 (s, 6H).

b) 4,5-Bis(anilino)phthalic acid dim ethyl ester

A solution of 5.6 g (15 mmol) of 4,5-bis (trimethylsilyloxy)cyclohexa 1,4-diene- 1,2-dicarboxylic acid dimethyl ester and 5.5 ml (60 mmol) of aniline in 60 ml of glacial acetic acid is boiled under reflux for 4 hours. The reaction mixture is cooled, the solvent is evaporated off and the dark-brown residue is dissolved in dichloromethane and the solution is washed in succession with 20 ml of 1N HCl, 50 ml of saturated NaHCO$_3$ and twice with 20 ml of water, dried With sodium sulfate and concentrated by evaporation. The crude product is recrystallized from ethanol, yielding the title compound in the form of yellow crystals, m.p. 178°, FAB-MS: 377 [M$^+$+H].

Alternatively the following procedure was used:

EXAMPLE 1'

4,5-Bis(anilino)phthalimide

A suspension of 21.9 g (66.3 mmol) of 4,5-bis(anilino) phthalic anhydride in 60 ml of formamide under argon atmosphere is heated at 125°–130° for 5 hours. The reaction mixture is cooled to 70°, and 250 ml of water are slowly added. This mixture is cooled to 0° for 30 minutes, and the reddish crystals are filtered off, washed with water and dried. Recrystallization from DMF/water yields the title compound in the form of orange crystals, m.p. 205°–207° C., FAB-MS: 330 [M$^+$+H].

a) 4,5-Bis(anilino)phthalic anhydride

A steady stream of argon is passed through a suspension of 23.4 g (67.18 mmol) of 4,5-bis(anilino)phthalic acid in 250 ml of toluene, and 19.0 ml(201.5 mmol, 3 eq) of acetic anhydride is added. The reaction mixture is heated to 60°–65° for 90 minutes with vigorous stirring. The reaction mixture is cooled to 10° for 30 minutes, and the yellow to orange crystals are filtered off and washed with toluene/hexane to yield the title compound in the form of yellow crystals, FAB-MS: 331 [M$^+$+H].

b) 4,5-Bis(anilino)phthalic acid

A steady stream of argon is passed through a suspension of 26.35 g (70.0 mmol) of 4,5-bis(anilino)phthalic acid dimethylester in 230 ml of methanol, and a solution of 11.78 g (280 mmol, 2 eq) of lithium hydroxide monohydrate in 116 ml of water is added. The reaction mixture is heated to reflux for 2.5 h, cooled to RT and diluted with 400 ml water. Methanol is removed by evaporation, the resulting solution is cooled to 0°, and 70 ml 4N hydrochloric acid are added. After 15 min. at 0°, the gray crystals are filtered off, washed with water and resuspended twice in 200 ml toluene with removal of the toluene by distillation to yield the title compound in the form of gray crystals, FAB-MS: 349 [M$^+$+H].

EXAMPLE 2

5,8-Diphenyl-5,8-diaza-5,6,7,8-tetrahydronaphthalene-2,3-dicarboxylic acid imide Analogously to Example 1, 40 mg (0.1 mmol) of 5,8-diphenyl-5,8-diaza-5,6,7,8-tetrahydronaphthalene-2,3-dicarboxylic acid dimethyl ester in 4 ml of ethylene glycol are heated at 120°, ammonia gas being passed through the mixture, with stirring, for 24 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with dichloromethane/methanol 20:1 and the product fractions are combined and concentrated by evaporation, yielding the title compound in the form of yellow crystals, FAB-MS: 356 [M$^+$+H].

a) 5,8-Diphenyl-5,8-diaza-5,6,7,8-tetrahydronaphthalene-2,3-dicarboxylic acid dimethyl ester A solution of 2.24 g (6 mmol) of 4,5-bis(trimethylsilyloxy)cyclohexa-1,4-diene-1,2-dicarboxylic acid dimethyl ester (Example 1a) and 5.1 g (24 mmol) of N,N'-diphenylethylenediamine in 24 ml of glacial acetic acid is boiled under reflux for 2 hours. The reaction mixture is cooled, the solvent is evaporated off and the dark-brown residue is dissolved in dichloromethane and the solution is washed in succession with 20 ml of 1N HCl, 50 ml of saturated NaHCO$_3$ and twice with 20 ml of water, dried with sodium sulfate and concentrated by evaporation. The crude product is chromatographed on silica gel with hexane/ethyl acetate 3:1 and the product fractions are concentrated by evaporation and the residue is recrystallized from ethanol, yielding the title compound in the form of orange crystals, FAB-MS: 402 [M$^+$], 403 [M$^+$+H].

EXAMPLE 3

4,5-Bis(4-fluoroanilino)phthalimide

Analogously to Example 1, 290 mg (0.7 mmol) of 4,5-bis(4-fluoroanilino)phthalic acid dimethyl ester in 22 ml of ethylene glycol are heated at 120° and, with stirring, ammonia gas is passed through the mixture for 18 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with hexane/ethyl acetate 1:1 and the product fractions are combined and concentrated by evaporation, yielding the title compound in the form of orange crystals, m.p.>220° C., FAB-MS: 366 [M$^+$+H].

a) 4,5-Bis(4-fluoroanilino)phthalic acid dimethyl ester

A solution of 2.4 g (6 mmol) of 4,5-bis(trimethylsilyloxy)cyclohexa-1,4-diene-1,2-dicarboxylic acid dimethyl ester (Example 1a) and 2.3 ml (24 mmol) of 4-fluoroaniline in 60 ml of glacial acetic add is boiled under reflux for 2 hours. The reaction mixture is cooled, the solvent is evaporated off and the dark-brown residue is dissolved in dichloromethane the solution is washed in succession with 20 ml of 1N HCl, 50 ml of saturated NaHCO$_3$ and twice with 20 ml of water, dried with sodium sulfate and concentrated by evaporation. The evaporation residue is chromatographed on silica gel with ethyl acetate/hexane 2:1 and the product fractions are concentrated by evaporation and recrystallized from ethyl acetate/hexane, yielding the title compound in the form of yellow crystals, $^1$H-NMR (CDCl$_3$): δ7.40 (s, 2H), 7.10–6.80 (m, 8H), 5.70 (br s, 2H) 3.83 (s, 6H).

Alternatively the following procedure was used:

EXAMPLE 3'

4,5-Bis(4-fluoroanilino)phthalimide

A suspension of 1000 mg (2.73 mmol) of 4,5-bis(4-fluoroanilino)phthalic anhydride in 5 ml of formamide under argon atmosphere is heated at 125°–130° for 5 hours. The reaction mixture is cooled to 60°, and 20 ml of water are slowly added. This mixture is cooled to 0° for 3 hours, and the reddish crystals are filtered off, washed with water and dried. Recrystallization from dichloromethane yields the title compound in the form of orange crystals, m.p. 244°–246° C., FAB-MS: 366 [M$^+$+H].

a) 4,5-Bis(4-fluoroanilino)phthalic anhydride

A steady stream of argon is passed through a suspension of 4.49 g (11.68 mmol) of 4,5-bis(4-fluoroanilino)phthalic acid in 75 ml of toluene and 3.32 ml (35.12 mmol, 3 eq) of acetic anhydride is added. The reaction mixture is heated to 60°–65° for 90 minutes with vigorous stirring. The reaction mixture is cooled to 10° for 15 minutes, the yellow orange crystals are filtered off and washed with toluene/hexane to yield the title compound in the form of yellow orange crystals, FAB-MS: 367 [M$^+$+H].

b) 4,5-Bis(4-fluoroanilino)phthalic acid

A steady stream of argon is passed through a suspension of 5.0 g (12.12 mmol) of 4,5-bis-(4-fluoroanilino)phthalic acid dimethylester in 40 ml of methanol, and a solution of 2.04 g (48.6 mmol, 2 eq) of lithium hydroxide monohydrate in 20 ml of water is added. The reaction mixture is heated to reflux for 1 hour, cooled to RT and diluted with 50 ml water. Methanol is removed by evaporation, the resulting solution is cooled to 0°, and 12 ml 4N hydrochloric acid and thereafter 100 ml of water are added. After 15 rain at 0°, the gray crystals are filtered off, washed with water and resuspended twice in 100 ml toluene with removal of the toluene by distillation to yield the title compound in the form of gray crystals, FAB-MS: 385 [M$^+$+H].

EXAMPLE 4

4,5-Bis(4-benzyloxy-anilino)phthalimide

Analogously to Example 1, 294.4 mg (0.5 mmol) of 4,5-bis(4-benzyloxy-anilino)phthalic acid dimethyl ester in 22 ml of ethylene glycol are heated at 120°, ammonia gas being passed through the mixture, with stirring, for 16 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with dichloromethane/methanol 50:1 and the product fractions are combined and concentrated by evaporation, yielding the title compound in the form of red crystals, m.p.187°–189° C., FAB-MS: 542 [M$^+$+H].

a) 4,5-Bis(4-benzyloxy-anilino)phthalic acid dimethyl ester

A solution of 2.4 g (6 mmol) of 4,5-his (trimethylsilyloxy) cyclohexa-1,4-diene-1,2-dicarboxylic acid dimethyl ester (Example 1a) and 4.8 g (24 mmol) of 4-benzyloxyaniline in 24 ml of glacial acetic acid is boiled under reflux for 2 hours. The reaction mixture is cooled, the solvent is evaporated off and the dark-brown residue is dissolved in dichloromethane and the solution is washed in succession with 20 ml of 1N HCl, 50 ml of saturated NaHCO$_3$ and twice with 20 ml of water, dried with sodium sulfate and concentrated by evaporation. The evaporation residue is dissolved while hot in ethyl acetate and filtered, then allowed to crystallize at 0°. The crystalline residue is chromatographed on silica gel with ethyl acetate/hexane 3:2 and the product fractions are concentrated by evaporation and recrystallized from ethyl acetate/hexane, yielding the title compound in the form of beige crystals, FAB-MS: 589 [M$^+$+H].

EXAMPLE 5

4,5-Bis[4-(N,N-diethylamino)-anilino]phthalimide bishydrochloride

Analogously to Example 1, 294.4 mg (0.5 mmol) of 4,5-bis[4-(N,N-diethylamino)anilino]phthalic acid dimethyl ester in 22 ml of ethylene glycol are heated at 120°, ammonia gas being passed through the mixture, with stirring, for 22 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with dichloromethane/methanol 30:1 and the product fractions are combined and concentrated by evaporation. The red crystalline evaporation residue is dissolved in dichloromethane, and 4.1N HCl (g) in ether is added thereto. The crystalline precipitate is filtered off and dried, yielding the title compound in the form of yellow crystals, m.p. 228°–230° C., FAB-MS: 472 [M$^+$+H].

a) 4,5-Bis[4-(N,N-diethylamino) anilino]phthalic acid dimethyl ester

A solution of 2.4 g (6 mmol) of 4,5-bis(trimethylsilyloxy) cyclohexa-1,4-diene-1,2-dicarboxylic acid dimethyl ester (Example 1a) and 3.94 g (24 mmol) of 4-(N,N-diethylamino)-aniline in 24 ml of glacial acetic acid is boiled under reflux for 2 hours. The reaction mixture is cooled, the solvent is evaporated off and the dark-brown residue is dissolved in dichloromethane and the solution is washed in succession with 50 ml of saturated NaHCO$_3$ and twice with 20 ml of water, dried with sodium sulfate and concentrated by evaporation. The evaporation residue is chromatographed on silica gel with dichloromethane/methanol 400:15 and the product fractions are concentrated by evaporation and again chromatographed on silica gel with ethyl acetate/hexane 1:1. The product fractions are concentrated by evaporation, yielding the title compound in the form of green crystals, FAB-MS: 518 [M$^+$], 519 [M$^+$+H].

EXAMPLE 6

4,5-Bis(cyclohexylamino)phthalimide

Analogously to Example 1, 194 mg (0.5 mmol) of 4,5-bis(cyclohexylamino)phthalic acid dimethyl ester in 15 ml of ethylene glycol are heated at 120°, ammonia gas being passed through the mixture, with stirring, for 12 hours. The reaction mixture is cooled, saturated with sodium chloride and extracted with ethyl acetate. The ethyl acetate phases are washed in succession three times with water and once with saturated sodium chloride solution, dried with sodium sulfate and concentrated by evaporation. The evaporation residue is chromatographed on silica gel with hexane/ethyl acetate 3:1 and the product fractions are combined and concentrated by evaporation, yielding the title compound in the form of orange crystals, m.p. 170°–175° C., FAB-MS: 342 [M$^+$+H].

a) 4,5-Bis(cyclohexylamino)phthalic acid dimethyl ester

A solution of 2.4 g (6 mmol) of 4,5-bis(trimethylsilyloxy) cyclohexa- 1,4-diene- 1,2-dicarboxylic acid dimethyl ester (Example 1a) in 21.5 ml (188 mmol) of cyclohexylamine and 4.5 ml of glacial acetic acid is boiled under reflux for 3.5 hours. The reaction mixture is cooled, the solvent is evaporated off and the dark-brown residue is dissolved in dichloromethane and the solution is washed in succession with 100 ml of 2N HCl, 50 ml of saturated NaHCO$_3$ and twice with 20 ml of water, dried with sodium sulfate and concentrated by evaporation. The evaporation residue is chromatographed on silica gel with ethyl acetate/hexane 5:12 and the product fractions are concentrated by evaporation and again chromatographed with ethyl acetate/hexane 1:4, yielding the title compound in the form of a yellow oil, FAB-MS: 388 [M$^+$].

4-Cyclohexylaminophthalic acid dimethyl ester is obtained as a secondary product and is converted into 4-cyclohexylaminophthalimide analogously to Example 6, yielding a colourless powder, FAB-MS: 245 [M$^+$], m.p. 217°–219° C.

EXAMPLE 7

4,5-Bis(4-methoxyanilino)phthalimide

Analogously to Example 1, 393 mg (0.9 mmol) of 4,5-bis(4-methoxyanilino)phthalic acid dimethyl ester in 25 ml of ethylene glycol are heated at 120°, ammonia gas being passed through the mixture, with stirring, for 18 hours. The reaction mixture is cooled, saturated with sodium chloride and extracted with ethyl acetate. The ethyl acetate phases are washed in succession three times with water and once with saturated sodium chloride solution, dried with sodium sulfate and concentrated by evaporation. The evaporation residue is chromatographed on silica gel with ethyl acetate/hexane 1:1 and the product fractions are combined and concentrated by evaporation, yielding the tire compound in the form of yellow crystals, m.p. 191°–193° C., FAB-MS: 390 [M$^+$+H].

a) 4,5-Bis(4-methoxyanilino)phthalic acid dimethyl ester

A solution of 2.4 g (6 mmol) of 4,5-bis(trimethylsilyloxy) cyclohexa-1,4-diene 1,2-dicarboxylic acid dimethyl ester (Example 1a) and 3.0 g (24 mmol) of 4-anisidine in 24 ml of glacial acetic acid is boiled under reflux for 2 hours. The reaction mixture is cooled, the solvent is evaporated off and the dark-brown residue is dissolved in dichloromethane and the solution is washed in succession with 20 ml of 1N HCl, 50 ml of saturated NaHCO$_3$ and twice with 20 ml of water, dried with sodium sulfate and concentrated by evaporation. The evaporation residue is chromatographed on silica gel with ethyl acetate/hexane 1:1 and the product fractions are concentrated by evaporation, yielding the title compound in the form of a yellow foam, FAB-MS: 437 [M$^+$+H].

EXAMPLE 8

4,5-Bis(2-iodoanilino)phthalimide

Analogously to Example 1, 1.48 g (2.36 mmol) of 4,5bis (2-iodoanilino)phthalic acid dimethyl ester in 25 ml of ethylene glycol are heated at 120° and, with stirring, ammonia gas is passed through the mixture for 19 hours. The reaction mixture is cooled, diluted with brine and extracted with ethyl acetate. The ethyl acetate phases are washed in succession three times with water and once with saturated sodium chloride solution, dried with sodium sulfate and concentrated by evaporation. The residue obtained after concentration by evaporation is filtered through silica gel with dichloromethane and the product fractions are combined and concentrated by evaporation. The residue obtained after concentration by evaporation is crystallized from boiling dichloromethane, yielding the title compound in the form of yellow crystals, m.p. 108°–110° C., FAB-MS: 582 [M$^+$+H].

a) 4,5-Bis(2-iodoanilino)phthalic acid dimethyl ester

A solution of 2.4 g (6 mmol) of 4,5-bis(trimethylsilyloxy) cyclohexa- 1,4-diene- 1,2-dicarboxylic acid dimethyl ester (Example 1a) and 5.3 g (24 mmol) of 2-iodoaniline in 24 ml of glacial acetic acid ii boiled under reflux for 2 hours. The reaction mixture is cooled, the solvent is evaporated off and the dark-brown residue is dissolved in dichloromethane and the solution is washed in succession with 20 ml of 1N HCl, 50 ml of saturated NaHCO$_3$ and twice with 20 ml of water, dried with sodium sulfate and concentrated by evaporation. The residue obtained after concentration by evaporation is chromatographed on silica gel with ethyl acetate/hexane 2:1 and the product fractions are concentrated by evaporation, yielding the title compound in the form of a yellow foam: $^1$H-NMR (DMSO-d$_6$): δ=7.91 (dxd, J$_1$=8, J$_2$=1, 2H) 7.39 (dxdxd, J$_1$=10, J$_2$=8, J$_3$=1, 2H), 7.32 (br s, 2H), 7.22–7.05 (m, 2H), 7.01 (s, 2H), 6.88 (txd, J$_f$=8, J$_d$=1, 2H), 3.73 (s,6H).

EXAMPLE 9

4,5-Bis(2-cyanoanilino)phthalimide

A solution of 581 mg (1 mmol) of 4,5-bis(2-iodoanilino) phthalimide and 197 mg (2.2 mmol) of copper(I) cyanide in DMF is stirred for 6 hours at 130°–140° C., the dark-brown solution changing into a dark-yellow suspension. The reaction mixture is cooled to 80° C. and diluted with 8 ml ethyl acetate. After further cooling to 60°–70° C., a solution of 467 mg (2.88 mmol) of iron(III) chloride in 1.6 ml of water and 300 μl of concentrated hydrochloric acid is added dropwise and the mixture is stirred for 30 minutes. 2 ml of water and Hyflo Super Cel® (kieselguhr from Fluka, Buchs, Switzerland) are added to the reaction mixture which is then filtered through Hyflo Super Gel® and the phases are separated. The aqueous phase is extracted once with ethyl acetate and the combined organic phases are washed twice with water, once with saturated sodium hydrogen carbonate solution and twice more with water, dried over magnesium sulfate and concentrated by evaporation. The resulting oily brown crystal mixture is chromatographed on silica gel with ethyl acetate/hexane 2:3. The product fractions are concentrated by evaporation and crystallized from boiling dichloromethane, yielding the title compound in the form of pale-yellow crystals: FAB-MS: 380 (M$^+$+H), m.p.: 279°–280° C.

5-Anilino-4-(2-cyanoanilino)phthalimide is obtained as a secondary product in the form of yellow crystals: FAB-MS: 355 (M$^+$+H), m.p.: 115°–117° C.

EXAMPLE 10

4,5-Bis(2-nitroanilino)phthalimide, 4-(4-nitroanilino)-5-(2,4-dinitroanilino)phthalimide and 4,5-bis(4-nitroanilino)phthalimide 990 mg (3 mmol) of 4,5-bis(anilino)phthalimide are added to a mixture of 12 mmol of acetic anhydride and 24 mmol of glacial acetic acid and 7.5 mmol of nitric acid (100%) at temperatures of less than 20° C. After stirring for 20 minutes, the reaction mixture is poured onto ice and extracted with ethyl acetate. The organic phases are washed once with saturated NaHCO$_3$ solution and once with water, dried over sodium sulfate and filtered. Chromatography twice on silica gel using a gradient of dichloromethane/ethyl acetate 1:1 to 3:1 yields the following amorphous compounds: 4,5-bis(2-nitroanilino)phthalimide in the form of a reddish-black powder: m.p. 87°–90° C.; 4-(4-nitroanilino)-5-(2,4-dinitroanilino)phthalimide in the form of a reddish-black powder:. m.p. 176°–178° C., $^1$H-NMR (DMSO-d$_6$): δ9.25 (s, 2H), 8.85 (d, J=2.5, 1H), 8.16 (dxd, J$_1$=8, J$_2$2.5, 1H), 8.13 (d, j=9, 2H), 7.88 (s, 1H), 7.75 (s, 1H), 7.17 (d, J=9, 2H), 6.96 (d, J=9.5, 1H) 4,5-bis(4-nitroanilino) phthalimide in the form of a red, lustrous powder: m.p. >250° C., decomposition from ~105° C., $^1$H-NMR (DMSO-d$_6$): 9.22 (br s, 2H), 8.12 (d, J=9.1, 4H ), 7.71 (s, 2H), 7.13 (d, J=9.1, 4H); $^{13}$C-NMR (DMSO-d$_6$): 168.9 s, 149.8 s, 139.6 s, 138.2s, 128.2 s, 125.9 d, 116.2 d, 115.6 d.

EXAMPLE 11

4,5-Bis(4-aminoanilino)phthalimide

A solution of 38 mg (0.09 mmol) of 4,5-bis(4-nitroanilino)phthalimide in 15 ml of THF is hydrogenated with 10% Raney nickel as catalyst for three hours at normal pressure and room temperature. The catalyst is filtered off and the reaction mixture is concentrated by evaporation, yielding the title compound in the form of a slightly yellowish powder: m.p. 154°–157° C., FAB-MS: 360 (M$^+$+H).

EXAMPLE 12

Analogously to the Example given in parentheses after each compound there are prepared:

(a) 4,5-Bis(4-iodoanilino)phthalimide, FAB-MS: 582 (M$^+$+H), m.p.: 246°–247° C. (analogously to Example 8)

(b) 4,5-Bis(3-iodoanilino)phthalimide, FAB-MS: 582 (M$^+$+H), m.p.: 244°–245° C. (analogously to Example 8)

(c) 4,5-Bis(2,6-dibromoanilino)phthalimide, FAB-MS: 642 (M$^+$+H), m.p.: 235°–237° C. (analogously to Example 8)

(d) 4,5-Bis(3-methoxyanilino)phthalimide, FAB-MS: 390 (M$^+$+H), m.p.: 169°–171° C. (analogously to Example 7):

(e) 4,5-Bis(2-methoxyanilino)phthalimide, FAB-MS: 390 (M$^+$+H), m.p.: 227°–228° C. (analogously to Example 7)

(f) 4,5-Bis(4-trifluoromethylanilino)phthalimide, FAB-MS: 512 (M$^+$+H), $^1$H-NMR (CD$_3$OD): 7.7 (s, 2H), 7.5 (d, 4H), 7.2 (d, 4H) (analogously to Example 1), (g) 4-Cyanoanilino-5-trifluoromethylanilino-phthalimide, FAB-MS: 423 (M$^+$+H), $^1$H-NMR (CDCl$_3$): 7.7 (d, 2H), 7.6 (d, 4H), 7.1 (d, 2H), 7.0 (d, 2H), 6.2 (s, 1H), 6.1 (s, 1H) (analogously to Example 1)

(h) 4,5-Bis(4-biphenylamino)phthalimide, FAB-MS: 482 (M$^+$+H), m.p.: 230°–231° C. (analogously to Example 1)

(i) 4,5-Bis(4-cyanoanilino)phthalimide, FAB-MS: 380 (M$^+$+H), m.p.:>250° C., $^1$H-NMR (DMSO-d$_6$): 7.1 (d, 4H), 7.6 (d, 4H), 7.7 (s, 2H) (analogously to Example 9)

(j) 4,5-Bis(3-cyanoanilino)phthalimide, FAB-MS: 380 (M$^+$+H), m.p.: 255°–257° C. (analogously to Example 9)

(k) 4,5-Bis(4-pyridineamino)phthalimide (analogously to Example 1)

(l) 4,5-Bis(3-pyridineamino)phthalimide (analogously to Example 1)

(m) 4,5-Bis(2-pyridineamino)phthalimide (analogously to Example 1)

(n) 4,5-Bis(2-pyrimidineamino)phthalimide (analogously to Example 1)

(o) 4,5-Bis(3-pyrimidineamino)phthalimide (analogously to Example 1)

(p) 4,5-Bis(4-pyrimidineamino)phthalimide (analogously to Example 1)

(q) 4,5-Bis(2-triazineamino)phthalimide (analogously to Example 1)

(r) 4,5-Bis(3-fluoroanilino)phthalimide (analogously to Example 3)

(s) 4,5-Bis(2-fluoroanilino)phthalimide (analogously to Example 3)

(t) 4,5-Bis(pentafluoroanilino)phthalimide (analogously to Example 3)

(u) 4,5-Bis(4-hydroxyanilino)phthalimide (analogously to Example 1)

(v) 4,5-Bis(3-hydroxyanilino)phthalimide (analogously to Example 1)

(w) 4,5-Bis(2-hydroxyanilino)phthalimide (analogously to Example 1)

(x) 4,5-Bis(4-ethylanilino)phthalimide (analogously to Example 1)

(y) 4,5-Bis(3-ethylanilino)phthalimide (analogously to Example 1)

(z) 4,5-Bis(2-ethylanilino)phthalimide (analogously to Example 1)

(aa) 4,5-Bis(3-methylanilino)phthalimide (analogously to Example 1)

(ab) 4,5-Bis(2-methylanilino)phthalimide (analogously to Example 1)

(ac) 4,5-Bis(3-trifluoromethylanilino)phthalimide (analogously to Example 1)

(ad) 4,5-Bis(2-trifluoromethylanilino)phthalimide (analogously to Example 1)

(ae) 4,5-Bis[4-(N,N-dimethylamino)-anilino]phthalimide (analogously to Example 5)

(af) 4,5-Bis[4-(N-acetylamino)-anilino]phthalimide (analogously to Example 1)

(ag) 4,5-Bis(3-biphenylylamino)phthalimide (analogously to Example 1)

(ah) 4,5-Bis(2-biphenylylamino)phthalimide (analogously to Example 1)

(ai) 4,5-Bis(1-naphthylamino)phthalimide (analogously to Example 1)

(aj) 4,5-Bis(2-naphthylamino)phthalimide (analogously to Example 1)

(ak) 4,5-Bis(5-tetralinylamino)phthalimide (analogously to Example 1)

(al) 4,5-Bis(4-carboxyanilino)phthalimide (analogously to Example 1)

(am) 4,5-Bis(3-carboxyanilino)phthalimide (analogously to Example 1)

(an) 4,5-Bis(2-carboxyanilino)phthalimide (analogously to Example 1)

(ao) 4,5-Bis(4-methoxycarbonyl-anilino)phthalimide (analogously to Example 1)

(ap) 4,5-Bis(3-methoxycarbonyl-anilino)phthalimide (analogously to Example 1)

(aq) 4,5-Bis(2-methoxycarbonyl-anilino)phthalimide (analogously to Example 1)

(ar) 4,5-Bis(4-ethoxycarbonyl-anilino)phthalimide (analogously to Example 1)

(as) 4,5-Bis(3-ethoxycarbonyl-anilino)phthalimide (analogously to Example 1)

(at) 4,5-Bis(2-ethoxycarbonyl-anilino)phthalimide (analogously to Example 1)

(au) 4,5-Bis(4-isopropyloxycarbonyl-anilino)phthalimide (analogously to Example 1)

(av) 4,5-Bis(4-tert-butyloxycarbonyl-anilino)phthalimide (analogously to Example 1)

(aw) 4,5-Bis(4-carbamoyl-anilino)phthalimide (analogously to Example 1)

(ax) 4,5-Bis(4-N,N-dimethylcarbamoyl-anilino)phthalimide (analogously to Example 1)

(ay) 4,5-Bis(4-hydroxy-3-methylanilino)phthalimide (analogously to Example 1)

(ba) 4,5-Bis(2-hydroxy-5-methylanilino)phthalimide (analogously to Example 1).

EXAMPLE 13

4,5-Bis(N-methyl-N-phenylamino)phthalimide

Analogously to Example 1, 66 mg (0.16 mmol) of 4,5-bis(N-methyl-N-phenylamino)phthalic acid dimethyl ester (Example 14 A) in 5 ml of ethylene glycol are heated at 120° and, with stirring, ammonia gas is passed through the mixture for 18 hours. The reaction mixture is cooled, and extracted with ethyl acetate. The ethyl acetate phases are washed in succession three times with water and once with saturated sodium chloride solution, dried with sodium sulfate and concentrated by evaporation. The evaporation residue is chromatographed on silica gel with hexane/ethyl acetate 1:1 and the product fractions are combined and concentrated by evaporation, yielding the title compound in the form of slightly yellow crystals, FAB-MS: 358 [M$^+$+H], $^1$H-NMR (CDCl$_3$): 3.05 (s, 6H).

EXAMPLE 14

4-(N-Methyl-N-phenylamino)-5-anilino-phthalimide

Analogously to Example 1, 160 mg (0.41 mmol) of 4-(N-methyl-N-phenylamino)-5-anilinophthalic acid dimethyl ester in 12 ml of ethylene glycol are heated at 120° and, with stirring, ammonia gas is passed through the mixture for 18 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with hexane/ethyl acetate 1:1 and the product fractions are combined and concentrated by evaporation, yielding the title compound in the form of slightly yellow crystals, FAB-MS: 344 [M$^+$+H], $^1$H-NMR (CDCl$_3$): 3.28 (s, 3H).

a) 4,5-Bis(N-methyl-N-phenylamino)phthalic acid dimethyl ester (A) and 4-(N-methyl-N-phenylamino)-5-anilino-phthalic acid dimethyl ester (B)

A solution of 564 mg (1.5 mmol) of 4,5-bis(anilino) phthalic acid dimethyl ester (Example 1) in 5 ml of acetonitrile is heated at 80° C. for 16 hours with 0.93 ml (15 mmol) of methyl iodide and 442 mg (3.2 mmol) of anhydrous potassium carbonate in a bomb tube. The reaction mixture is concentrated to dryness by evaporation, the residue is twice digested in dichloromethane and filtered, and the filtrate is concentrated by evaporation. Repeated chromatography on silica gel with hexane/ethyl acetate yields the title compounds in the form of slightly yellowish powders. (A): FAB-MS: 405 [M$^+$+H]; (B): FAB-MS: 391 [M$^+$+H].

EXAMPLE 15

4,5-Bis(anilino)-N(2!-methyl-phthalimide

Analogously to Example 1, 376 mg (1 mmol) of 4,5-bis (anilino)phthalic acid dimethyl ester in 33 ml of ethylene glycol are heated at 120° and, with stirring, methylamine is passed through the mixture for 18 hours. The reaction mixture is cooled and extracted with ethyl acetate. The ethyl acetate phases are washed in succession three times with water and once with saturated sodium chloride solution, dried with sodium sulfate and concentrated by evaporation. The evaporation residue is chromatographed on silica gel with hexane/ethyl acetate 1:1 and the product fractions are combined and concentrated by evaporation, yielding the title compound in the form of slightly yellow crystals, FAB-MS: 344 [M$^+$+H], m.p. 195°–196° C.

EXAMPLE 16

4,5-Bis(anilino)-thiophthalimide [=5,6-bis(anilino)-isoindol-1-one-3-thione]

138 mg (0.36 mmol) of Lawesson reagent [=2,4-bis(4-methoxyphenyl)-2,4-dithioxo-1,3,2,4-dithiaphosphetane] are added to a solution of 100 mg (0.3 mmol) of 4,5-bis (anilino)phthalimide (Example 1) in 15 ml of dichloromethane and the mixture is boiled under reflux for 4 hours. The reaction mixture is concentrated by evaporation and chromatographed directly on silica gel with hexane/ ethyl acetate 2:1. The product fractions are concentrated by evaporation, yielding the title compound in the form of yellow crystals, FAB-MS: 346 [M$^+$+H].

EXAMPLE 17

4,5-Bis(anilino)-N$^4$, N$^5$-propane-1,3-diyliphthalimide, 4-(N-allyl-N-phenyl)amino-5-anilinophthalimide and 4,5-Bis(anilino)-N$^4$, N$^5$-propane-1,3-diyl-N-methylphthalimide In an autoclave, 417 mg (1 mmol) of 4,5-bis(anilino)-N$^4$, N$^5$-propane-1,3-diyl-phthalic acid dimethyl ester are dissolved in 5 ml of methanol, and 15 ml of ammonia are used for the purpose of amide formation. The autoclave is closed and then heated at 120° C. for 24 hours, then cooled and opened, and the ammonia is driven off with nitrogen. The residue is rinsed out with ethyl acetate and filtered, and the filtrate is chromatographed on silica gel with hexane/ethyl acetate 3:1. The product fractions are concentrated by evaporation and crystallized from hexane/ethyl acetate, yielding the title compound in the form of yellow crystals, FAB-MS: 370 [M$^+$+H], m.p. 230°–233° C. As byproduct of the reaction, 4-(N-allyl-N-phenyl)amino-5-anilinophthalimide was isolated and recrystallized from hexane/ethyl acetate to yield yellow crystals, FAB-MS: 370 [M$^+$+H], m.p. 140°–147° C. As further byproduct of the reaction, 4,5-Bis(anilino)-N$^4$, N$^5$-propane-1,3-diyl-N-methylphthalimide was isolated and recrystallized from hexane/ethyl acetate to yield yellow crystals, FAB-MS: 384 [M$^+$+H], m.p. 247° C.

EXAMPLE 18

4,5-Bis(N-allyl-N-phenylamino)phthalimide

In an autoclave, 457 mg (1 mmol) of 4,5-bis(N-allylanilino)phthalic acid dimethyl ester are dissolved in 5 ml of methanol, and 15 ml of ammonia are Used for the purpose of amide formation. The autoclave is closed and then heated at 120° C. for 24 hours, then cooled and opened, and the ammonia is driven off with nitrogen. The residue is rinsed out with ethyl acetate and filtered, and the filtrate is chromatographed on silica gel with hexane/ethyl acetate 3:1. The product fractions are concentrated by evaporation and crystallized from hexane/ethyl acetate, yielding the title compound in the form of yellow crystals, FAB-MS: 410 [M$^+$+H], m.p. 122°–127° C. As byproduct of the reaction, 4,5-Bis-(N-allyl-N-phenylamino)phthalic acid monoamide was isolated and recrystallized from hexane/ethyl acetate to yield yellow crystals, FAB-MS: 428 [M$^+$+H], m.p. 114°–116° C.

a) 4,5-Bis(anilino)-N$^4$, N$^5$-propanediyl-phthalic acid dimethyl ester and 4,5-bis(N-allylanilino)phthalic acid dimethyl ester 0.6 g (15.4 mmol) of sodium amide is added at room temperature under argon to a solution of 3.76 g (10 mmol) of 4,5-bis(anilino)phthalic acid dimethyl ester (Example 1) in 15 ml of HMPT (hexamethylphosphoric acid triamide) or DMPU, and the mixture is heated at 60° C. for 30 minutes. The deep red solution is cooled to room temperature and evacuated for 5 minutes (1 torr), then a solution of 1.5 ml (15.2 mmol) of 1-bromo-3-chloropropane in 2 ml of THF is added dropwise and the reaction mixture is stirred for 18 hours at room temperature. The reaction mixture is poured onto ice-water, extracted with ethyl acetate and the organic phases are combined and washed with generous amounts of water, dried over sodium sulfate and concentrated by evaporation. The evaporation residue is chromatographed on silica gel with hexane/ethyl acetate 5:1, yielding the title compounds: 4,5-bis(anilino)-N$^4$, N$^5$-propanediyl-phthalic acid dimethyl ester in the form of colourless crystals, FAB-MS: 417 [M$^+$+H]; and 4,5-bis(N-allylanilino)phthalic acid dimethyl ester in the form of a colourless oil, FAB-MS: 457 [M$^+$+H].

EXAMPLE 19

Analogously to Examples 13–18 there are prepared:

(a) 4-(N-Acetyl-N-phenyl)amino 5-anilino-phthalimide, FAB-MS: 372 [M$^+$+H], $^1$H-NMR (DMSO-d$_6$): 2.05 (s, 3H) (analogously to Example 14)

(b) 4,5-Bis(anilino)-N-benzyl-phthalimide (analogously to Example 15)

EXAMPLE 20

5000 capsules are prepared, each comprising 0.25 g of active ingredient, for example one of the compounds prepared in Examples 1 to 16:

| Composition | |
|---|---|
| active ingredient | 1250 g |
| talc | 180 g |
| wheat starch | 120 g |
| magnesium stearate | 80 g |
| lactose | 20 g |

Method

The pulverulent substances are forced through a sieve having a mesh size of 0.6 mm and mixed together. 0.33 g portions of the mixture are filled into gelatin capsules using a capsule-filling machine.

EXAMPLE 21

5000 weak gelatin capsules are prepared, each comprising 0.05 g of active ingredient, for example one of the compounds prepared in Examples 1 to 16:

| Composition | |
|---|---|
| active ingredient | 250 g |
| lauroglycol | 2 l |

Method

The pulverulent substance is suspended in Lauroglycol (propylene glycol laurate, Gattefossé S. A., Saint Priest, France) and grinded in a wet pulverizer to a size of 1–3 μm. Portions of 0.419 g each of the mixture are filled into soft gelatin capsules using a capsule-filling machine.

EXAMPLE 22

5000 soft gelatin capsules are prepared, each comprising 0.05 g of active ingredient, for example one of the compounds prepared in Examples 1 to 16:

| Composition | |
|---|---|
| active ingredient | 250 g |
| PEG 400 | 1 l |
| Tween 80 | 1 l |

Method

The pulverulent substance is suspended in PEG 400 (polyethylene glykol with $M_r$ between about 380 and 420, Fluka, Switzerland) and ®Tween 80 (Polyoxyethylene-sorbitane-monolaurate, Atlas Chem. Ind., Inc, USA, provided by Fluka, Switzerland) and grinded in a wet pulverizer to a size of 1–3 μm. 0.43 g portions of the mixture are filled into soft gelatin capsules using a capsule-filling machine.

EXAMPLE 23

4-Anilino-5-(4-hydroxy-anilino)-phthalimide

To a solution of 359.4 mg (1 mmol) of 4-anilino-5-(4-methoxy-anilino)-phthalimide in 5 ml of chloroform, a solution of 186 μl (2 mmol) boron tribromide is added dropwise at −40° C. to −30° C. The reaction mixture is stirred for 5 hours at −30° C., and is then quenched with 5 ml of water. The reaction mixture is warmed up to room temperature, and the phases are separated. The organic phase is washed twice with water, dried over magnesium sulfate and concentrated by evaporation. Excluding light, the evaporation residue is chromatographed with ethylacetate/hexane 1:1 on a silica gel column that is cooled with ice-water (double jacket), the product fractions are combined and concentrated by evaporation. The title compound is obtained in the form of yellow crystals, FAB-MS: 346 [$M^+$+H].

a) 4-Anilino-5-(4-methoxy-anilino)pthalimid

Analogously to Example 1, 0.7 g (1.7 mmol) 4-anilino-5-(4-methoxy-anilino)-phthalic acid dimethyl ester are heated at 120°, ammonia gas being passed through the mixture, with stirring, for 18 hours. The reaction mixture is cooled and extracted with ethyl acetate. The ethyl acetate phases are washed in succession twice with water and once with saturated sodium chloride solution and dried with magnesium sulfate and concentrated by evaporation. The evaporation residue is chromatographed on silica gel with ethyl acetate/hexane 1:1 and the product fractions are combined and concentrated by evaporation, yielding the title compound in the form of yellow crystals, m.p. 266°–7° C., FAB-MS: 360 [$M^+$+H].

b) 4-Anilino-5-(4-methoxy-anilino)-phthalic acid dimethyl ester and 4,5-Bis(4-methoxyanilino)-phthalic acid dimethyl ester A solution of 4.8 g (12 mmol) 4,5-Bis(trimethylsilyloxy) cyclohexa-1,4-diene 1,2-dicarboxylic acid dimethyl ester (Example 1 a), 2.6 g (24 mmol) p-anisidine and 2.2 ml (24 mmol) aniline in 48 ml of glacial acetic acid is boiled under reflux for 2 hours. The reaction mixture is cooled, the solvent is evaporated and the dark-brown residue is dissolved in ethyl acetate and the solution is washed in succession with 40 ml of 1N HCl 100 ml of saturated $NaHCO_3$ and twice with water, dried with magnesium sulfate and concentrated by evaporation. The evaporation residue is chromatographed on silica gel with ethyl acetate/hexane 1:3 and the product fractions are concentrated by evaporation. This way, in the first product fractions 4,5-bis-(4-methoxyanilino)-phthalic acid dimethyl ester is obtained in the form of a yellow foam: FAB-MS: 437 [$M^+$+H]. The evaporation residue of the product fractions following thereafter is recrystallized, and 4-anilino-5-(4-methoxy-anilino)-phthalic acid dimethyl ester is obtained in the form of yellow crystals, m.p. 122°–4° C., FAB-MS: 407 [$M^+$+H].

EXAMPLE 24

4-Anilino-5-(2,4-dihydroxy-anilino)-phthalimide

To a solution of 100 mg (0.26 mmol) of 4-anilino-5-(2, 4-dimethoxy-anilino)-phthalimide in 8 ml of chloroform, a solution of 120 μl (1.24 mmol) boron tribromide is added dropwise at RT. The reaction mixture is stirred for 5 hours at RT, is then quenched with 5 ml of water and the phases are separated. The water phase is extracted three times with ethyl acetate. The organic phases are combined and washed twice with water, dried over magnesium sulfate and concentrated by evaporation. Excluding light, the evaporation residue is chromatographed with ethylacetate/hexane 2:1 on a silica gel column (precoated with 0.1 g of sodium ascorbate per g silica gel) that is cooled with ice-water (double jacket), the product fractions are combined and concentrated by evaporation. Recrystallization from ethyl acetate/dichloromethane/hexane yields the title compound in the form of yellow crystals, m.p. 155° C. (decomp.), FAB-MS: 362 [$M^+$+H].

a) 4-Anilino-5-(2,4-dimethoxy-anilino)pthalimide (this compound is also an endproduct of formula I)

A steady stream of argon is passed through a suspension of 386 mg (0.945 mmol) of 4-anilino-5-(2,4-dimethoxy-anilino)phthalic acid in 3.5 ml of toluene and 268μl (2.835 mmol, 3 equivalents) of acetic anhydride is added. The reaction mixture is heated to 60°–65° for 4 hours. The reaction mixture is cooled and concentrated by evaporation, resuspended in 7 ml of formamide under argon atmosphere and heated at 125°–130° for 20 hours. The reaction mixture is cooled to RT and water is added. The mixture is extracted with ethyl acetate. The ethyl acetate phases are washed in succession twice with water and once with saturated sodium chloride solution and dried with magnesium sulfate and concentrated by evaporation. The evaporation residue is chromatographed on silica gel with ethyl acetate/hexane 1:1 and the product fractions are combined and concentrated by evaporation. Crystallization from dichloromethane/hexane yields the title compound in the form of yellow crystals, m.p. 193°–5° C., FAB-MS: 390 [M$^+$+H].

b) 4-Anilino-5-(2,4-dimethoxy-anilino)phthalic acid

A steady stream of argon is passed through a suspension of 479 mg (1.09 mmol) of 4-anilino-5-(2,4-dimethoxy-anilino)phthalic acid dimethylester in 3.6 ml of methanol, and a solution of 205 mg (4.905 mmol, 4.5 eq) of lithium hydroxide monohydrate and 10 mg sodium ascorbate in 1.7 ml of water is added. The reaction mixture is heated to reflux for 4 hours, cooled to RT, and the methanol is removed by evaporation. The resulting mixture is poured onto 20 ml of 4N hydrochloric acid, the red suspension is filtered and the crystals are washed with washed with isopropanol/hexane 1:5 to yield the title compound in the form of red crystals, TLC (dichloromethane/methanol 7:3) R$_f$=0.33.

c) 4-Anilino-5-(2,4-dimethoxy-anilino)-phthalic acid dimethyl ester and 4,5-Bis(2,4-dimethoxy-anilino)-phthalic acid dimethyl ester A solution of 1.31 g (3 mmol) 4,5-Bis(trimethylsilyloxy) cyclohexa-1,4-diene-1,2-dicarboxylic acid dimethyl ester (Example 1a), 306 mg (3 mmol) pivalic acid and 1 ml of DMF is heated under argon to 120° and a solution of 460 mg (3 mmol) 2,4-dimethoxy-anilin in 1 ml of DMF is added within 5 minutes. The reaction mixture is heated at 120° for 10 minutes, cooled, diluted with water and extracted with ethyl acetate. The organic phase is washed in succession with 1N HCl water, saturated Na$_2$CO$_3$, water and brine, dried with magnesium sulfate and concentrated by evaporation. The evaporation residue, a brown oil, 402 mg (3.9 mmol) pivalic acid and 2 ml of ethanol are heated to reflux and a solution of 358 μl (3.9 mmol) of aniline in 3 ml of ethanol is added dropwise. The reaction mixture is heated to reflux for 15 hours, cooled, diluted with water and extracted with ethyl acetate. The organic phase is washed in succession with 1N HCl, water, saturated Na$_2$CO$_3$, water and bring, dried with magnesium sulfate and concentrated by evaporation. The evaporation residue is chromatographed on silica gel with ethyl acetate/hexane 1:2 and the product fractions are concentrated by evaporation. This way, in the first product fractions 4-anilino-5-(2,4-dimethoxy-anilino)-phthalic acid dimethyl ester is obtained in the form of a yellow oil: FAB-MS: 437 [M$^+$+H]. The evaporation residue of the product fractions following thereafter is recrystallized, and 4,5-bis-(2,4-dimethoxy-anilino)-phthalic acid dimethyl ester is obtained in the form of a yellow foam: FAB-MS: 497 [M$^+$+H].

EXAMPLE 25

4,5-bis(2,4-dimethoxy-anilino)-phthalimide

A suspension of 190 mg (0.46 mmol) of 4,5-bis(2,4-dimethoxy-anilino)-phthalic acid and 138 mg (2.3 mmol) of area in 8 ml of xylene is heated to reflux for 7 hours. The yellow suspension is cooled to RT and extracted with water. The water phase is extracted three times with ethyl acetate. The organic phases are combined and washed twice with water, dried over magnesium sulfate and concentrated by evaporation. Excluding light, the evaporation residue is chromatographed with ethylacetate/dichloromethane 1:19 on a silica gel column, and the product fractions are combined and concentrated by evaporation yielding the title compound in the form of red crystals, FAB-MS: 450 [M$^+$+H].

The starting materials are a) 4,5-bis(2,4-dimethoxy-anilino)phthalic acid

A steady stream of argon is passed through a suspension of 260 mg (0.6 mmol) of 4,5-bis(2,4-dimethoxy-anilino) phthalic acid dimethylester in 2 ml of methanol, and a solution of 101 mg (2.4 mmol, 4 eq) of lithium hydroxide monohydrate and 10 mg sodium ascorbate in 1 ml of water is added. The reaction mixture is heated to reflux for 10 hours, cooled to RT, and the methanol is removed by evaporation. The resulting mixture is poured onto 20 ml of 4N hydrochloric acid, the red suspension is filtered and the crystals are washed with washed with isopropanol/hexane 1:5 to yield the title compound in the form of red crystals, FAB-MS: 469 [M$^+$+H].

EXAMPLE 26

4-Anilino-5-(3,4-dihydroxy-anilino)-phthalimide

To a solution of 219 mg (0.56 mmol) of 4-anilino-5-(3,4-dimethoxy-anilino)-phthalimide in 5 ml of dichloromethane, a solution of 270 μl (2.8 mmol) boron tribromide in 3 ml of dichloromethane is added dropwise at RT. The reaction mixture is stirred for 5 hours at RT and then quenched with 5 ml of water, and the phases are separated. The water phase is extracted three times with ethyl acetate. The organic phases are combined and washed twice with water, dried over magnesium sulfate and concentrated by evaporation. Excluding light, the evaporation residue is chromatographed with ethylacetate/hexane 2:1 on a silica gel column (precoated with 0.1 g of sodium ascorbate per g silica gel) that is cooled with ice-water (double jacket), and the product fractions are combined and concentrated by evaporation. Recrystallization from ethyl acetate/ dichloromethane/hexane yields the title compound in the form of orange crystals, FAB-MS: 362 [M$^+$+H].

a) 4-Anilino-5-(3,4-dimethoxy-anilino)pthalimid (this compound is also an endproduct of formula I)

A steady stream of argon is passed through a suspension of 719 mg (1.65 mmol) of 4-anilino-5-(3,4-dimethoxy-anilino)phthalic acid dimethylester in 5.3 ml of methanol, and a solution of 312 mg (7.425 mmol, 4.5 eq) of lithium hydroxide monohydrate and 10 mg sodium ascorbate in 3 ml of water is added. The reaction mixture is heated to reflux for 2.5 hours, cooled to RT, and the methanol is removed by evaporation. 10 ml of water and 4 ml of 4N hydrochloric acid are added, and the water phase is extracted three times with ethyl acetate. The organic phases are combined and washed twice with water, dried over magnesium sulfate and concentrated by evaporation. The resulting yellow oil is resuspended in 5 ml of toluene, and 470 μl of acetic anhydride is added. The reaction mixture is heated to 80° for 3 hours. The reaction mixture is cooled and concentrated by evaporation, resuspended in 5 ml of formamide under argon atmosphere and heated at 125°–130° for 20 hours. The reaction mixture is cooled to RT and water is added. The mixture is extracted with ethyl acetate. The ethyl acetate phases are washed in succession twice with water and once with brine, dried with magnesium sulfate and concentrated by evaporation. The evaporation residue is chromatographed on silica gel with ethyl acetate/hexane 1:1, and the product fractions are combined and concentrated by evaporation. Crystallization from dichloromethane/hexane yields the title compound in the form of yellow crystals, m.p. 204°–5° C., FAB-MS: 390 [M$^+$+H].

b) 4-Anilino-5-(3,4-dimethoxy-anilino)-phthalic acid dimethyl ester and 4,5-Bis(3,4-dimethoxy-anilino)-phthalic acid dimethyl ester A solution of 2.8 g (6 mmol) 4,5-Bis(trimethylsilyloxy) cyclohexa-1,4-diene-1,2-dicarboxylic acid dimethyl ester (Example 1 a), 612 mg (6 mmol) pivalic acid and 1.53 g (10 mmol) 3,4-dimethoxy-anilin is heated to 120° for 1 hour, 550 µl (6 mmol) of aniline are then added. The reaction mixture is heated to 120° for 9 hours, cooled, diluted with water and extracted with ethyl acetate. The organic phase is washed in succession with 0.1N HCl water, saturated Na$_2$CO$_3$, water and brine, dried with magnesium sulfate and concentrated by evaporation. The evaporation residue is taken up in ethyl acetate, and the resulting crystals are filtered off yielding 4,5-bis-(3,4-dimethoxy-anilino)-phthalic acid dimethyl ester in the form of yellow crystals: FAB-MS: 497 [M$^+$+H]. The mother liquor is concentrated by evaporation, the residue chromatographed on silica gel with ethyl acetate/hexane 2:3, and the product fractions are concentrated by evaporation yielding 4-anilino-5-(3,4-dimethoxy-anilino)-phthalic acid dimethyl ester in the form of a yellow foam: FAB-MS: 437 [M$^+$+H].

EXAMPLE 27

4-Anilino-5-(3,4,5-trimethoxy-anilino)pthalimid

A steady stream of argon is passed through a suspension of 140 mg (0.32 mmol) of 4-anilino-5-(3,4,5-trimethoxy-anilino)phthalic acid in 1.2 ml of toluene and 90 µl (0.958 mmol, 3 eq) of acetic anhydride is added. The reaction mixture is heated to 60°–65° for 6 hours. The reaction mixture is cooled and concentrated by evaporation, resuspended in 7 ml of formamide under argon atmosphere and heated at 125°–130° for 15 hours. The reaction mixture is cooled to RT and water is added. The mixture is extracted with ethyl acetate. The ethyl acetate phases are washed in succession twice with water and once with saturated sodium chloride solution and dried with magnesium sulfate and concentrated by evaporation. The evaporation residue is chromatographed on silica gel with ethyl acetate/hexane 2:3 and the product fractions are combined and concentrated by evaporation. Crystallization from ethyl acetate yields the title compound in the form of yellow crystals, m.p. 203°–5° C., FAB-MS: 420 [M$^+$+H].

a) 4-anilino-5-(3,4,5-trimethoxy-anilino)phthalic acid

A steady stream of argon is passed through a suspension of 245 mg (0.5 mmol) of 4-anilino-5-(3,4,5-trimethoxy-anilino)phthalic acid dimethylester in 1.6 ml of methanol, and a solution of 94.4 mg (2.25 mmol, 4.5 eq) of lithium hydroxide monohydrate and 10 mg sodium ascorbate in 0.8 ml of water is added. The reaction mixture is heated to reflux for 17 hours and then cooled to RT. The resulting mixture is treated dropwise with 0.5 ml of 4N hydrochloric acid, the green suspension is filtered, and the crystals are washed with water to yield the title compound in the form of green crystals, m.p. 145°–6° C., FAB-MS: 439 [M$^+$+H].

b) 4-Anilino-5-(3,4,5-trimethoxy-anilino)-phthalic acid dimethyl ester

A solution of 3.92 g (9 mmol) 4,5-Bis(trimethylsilyloxy) cyclohexa-1,4-diene-1,2-dicarboxylic acid dimethyl ester (Example 1a), 918 mg (9 mmol) pivalic acid and 3 ml of DMF is heated under argon to 120° C., and a solution of 1.65 g (9 mmol) 3,4,5-trimethoxy-anilin in 3 ml of DMF is added within 5 minutes. The reaction mixture is heated at 120° for 10 minutes, cooled, diluted with water and extracted with ethyl acetate. The organic phase is washed in succession with 1N HCl water, saturated Na$_2$CO$_3$, water and brine, dried with magnesium sulfate and concentrated by evaporation yielding 2.54 g of a brown oil. 1.14 g of the evaporation residue, 230.5 mg (2.26 mmol) pivalic acid and 0.5 ml of ethanol are heated to reflux and a solution of 208 µl (2.26 mmol) of aniline in 0.5 ml of ethanol is added dropwise. The reaction mixture is heated to reflux for 15 hours, cooled, diluted with water and extracted with ethyl acetate. The organic phase is washed in succession with 1N HCl, water, saturated Na$_2$CO$_3$, water and brine, dried with magnesium sulfate and concentrated by evaporation. The evaporation residue is chromatographed on silica gel with ethyl acetate/hexane 1:1 and the product fractions are concentrated by evaporation, yielding 4-anilino-5-(3,4,5-trimethoxy-anilino)-phthalic acid dimethyl ester in the form of yellow crystals: FAB-MS: 467 [M$^+$+H].

EXAMPLE 28

4-Anilino-5-(3,4,5-trihydroxy-anilino)-phthalimide

To a suspension of 78 mg (0.18 mmol) of 4-anilino-5-(3,4,5-trimethoxy-anilino)phthalimide (Example 27) in 4 ml of dichloromethane, a solution of 314 µl (3.24 mmol) boron tribromide is added dropwise at RT. The reaction mixture is stirred for 4 hours at RT, is then cooled to 0° and quenched with 5 ml of water, and the phases are separated. The water phase is extracted three times with ethyl acetate. The organic phases are combined and washed twice with water, dried over magnesium sulfate and concentrated by evaporation. Excluding light, the evaporation residue is chromatographed with ethylacetate/dichloromethane 4:1 on a silica gel column (precoated with 0.4 g of sodium ascorbate per g silica gel) that is cooled with ice-water (double jacket), the product fractions are combined and concentrated by evaporation yielding the title compound in the form of dark red crystals, m.p. 152° C. (decomp.), FAB-MS: 378 [M$^+$+H].

EXAMPLE 29

Analogously to Examples 24–28 there are prepared:
(a) 4,5-Bis(3,4-dimethoxy-anilino)-phthalimide, FAB-MS: 450 [M$^+$+H](analogously to Example 25);
(b) 4,5-Bis(3,4-dihydroxy-anilino)-phthalimide, FAB-MS: 392 [M$^+$+H](analogously to Example 24);
(c) 4,5-Bis(2,4-dihydroxy-anilino)-phthalimide, FAB-MS: 392 [M$^+$+H](analogously to Example 24);
(d) 4,5-Bis(3,5-dimethoxy-anilino)-phthalimide, FAB-MS: 450 [M$^+$+H](analogously to Example 25);
(e) 4,5-Bis(3,5-dihydroxy-anilino)-phthalimide, FAB-MS: 392 [M$^+$+H](analogously to Example 24).

EXAMPLE 30

4,5-Bis(4-methylanilino)-phthalimide

Ammonia is passed through a solution of 4,5-bis(4-methylanilino)-phthalic acid anhydride (0.74 g) in 2-ethoxyethanol at 120° C. during 4 h. Evaporation follows, and the dark-coloured residue is freed from a polar, resinous residue by filtration over silica gel (eluent: ethyl acetate/hexane 1:1). The purified title compound, recrystallized from diethyl ether/pentane, forms orange-red, very firm crystals that melt at 233°–235° C. (decomp.). $C_{22}H_{19}N_3O_2$: molecular weight calculated 357, found 357 (FD-MS).

a) 4,5-bis(4-methylanilino)-phthalic acid anhydride 4,5-bis(4-methylanilino)-phthalic acid dimethylester (4.45 g, 0.011 mol) are heated with 50 ml 2M NaOH in water and 1000 ml methanol under reflux and nitrogen atmosphere. After that, the reaction mixture is evaporated to 300 ml and acidified with 5M HCl; the dicarbonic acid formed is extracted several times with ethyl acetate. The combined extracts are dried (disodium sulfate) and evaporated. The remaining brownish product is dissolved in acetic add anhydride and warmed to 40° C. during 10 min. After that, the mixture is evaporated again, and the residue is purified by filtration over silica gel (eluent: ethyl acetate/hexane 1:1). The crude title compound is obtained as intensively yellow-coloured filtrate. After evaporation; this crude product is re, crystallized from diethyl ether. The title compound is obtained: m.p. 221°–223° C. ; $C_{22}H_{28}N_{28}=_2$: molecular weight calculated 358, found 358 (FD-MS).

b) 4,5-bis(4-methylanilino)-phthalic acid dimethylester

Analogously to example 1b), the title compound is obtained starting from 23.1 g (60.8 mmol) of 4,5-bis(trimethylsilyloxy)cyclohexa-1,4-diene-1,2-dicarbonic acid dimethylester and 22.7 g (0.21 mmol) of 4-toluidine (Fluka, Buchs, Schweiz). The pure title compound is obtained after recrystallization from ethyl acetate/diethyl ether in the form of yellow, gleaming crystal platelets, m.p. 170°–172° C.

EXAMPLE 31

$N^{(2)}$-amino-4,5-dianilino-phthalimide 0.131 g of 4,5-dianilino-N-(4-methoxybenzyloxycarbonyl)-amino-phthalimide are hydrated in 8 ml of ethanol in the presence of palladium (10% on charcoal, 40 mg) at RT. After 4 h and an uptake of about 6 ml $H_2$, the catalyst is removed by filtration over siliceous earth, and the resulting solution, which is coloured yellow, is evaporated. The residue is purified on a silica gel column (eluent: hexane/ethyl acetate 1:1). After separation from yellowish impurities that are eluted first, the main quantity is isolated from a strong, yellow-coloured band. The title compound, after recrystallization from ethanol/diethyl ether, forms firm, orange to yellow prisms, m.p. 190°–193° C. $C_{20}H_{16}N_4O_2$: molecular weight calculated 344, found 344 (FD-MS).

a) 4,5-dianilino-N-(4-methoxybenzyloxycarbonyl)-amino-phthalimide

A solution of 4,5-dianilino-phthalic acid anhydride (0.250 g, 0.76 mmol) and hydrazine carbonic acid-(4-methoxybenzyl)ester (0.164 g, 0.84 mmol) in ethanol is boiled during 14 h under reflux. After evaporation, the reaction mixture is purified over a silica gel column. Elution with hexane/ethal acetate 2:1 and recrystallization from diethyl ether gives the title compound in pale-yellow prisms.

b) 4,5-dianilino-phthalic acid anhydride

A solution of 2 g of 4,5-dianilino-phthalic acid (Example 1'b)) in acetanhydride is heated to 60° C. for 30 min, resulting in a strong yellow colouring of the reaction mixture. After evaporation, yellow crystals of the crude title compound remain which are recrystallized from acetone/diethyl ether; the title compound has a m.p. of 196°–197° C. $C_{20}H_{14}N_2O_3$: molecular weight calculated 330, found 330 (FD-MS).

EXAMPLE 32

$N^{(2)}$-hydroxy-4,5-dianilino-phthalimide

To a solution of 4,5-dianilino-phthalic acid anhydride (0.147 g, Example 31 b)) in tetrahydrofuran (15 ml), an excess of hydroxylamine (1 ml of a 50% solution in water) is added, and the reaction mixture, which immediately becomes colourless, is evaporated to dryness, followed by heating of the dry residue to 100° C. for 45 min. During this procedure, the reaction mixture rapidly becomes orange-yellow. For purification, the material is chromatographed over silica gel with ethyl acetate as eluent. After separation from a light yellow band that is eluted before, the main fraction is obtained which contains the title compound as an orange-yellow material. $C_{20}H_{15}N_3O_3$: molecula weight calculated 345, found 345 (FD-MS).

EXAMPLE 33

4,5-dianilino-isoindolinone

A solution of 4,5-dianilino-monothiophthalimide (0.145 g; Example 34) in ethanol (30 ml) is hydrated during 4 h in the presence of Raney-Nickel as catalyst (3 g). The catalyst is removed (silaceous earth), the filtrate is evaporated, and the remaining yellowish residue is crystallized from diethyl ether/ethanol. The title compound is obtained in pale-yellow crystals, m.p. 225° C.

$C_{20}H_{17}N_3O$: molecular weight calculated 315, found 315 (FD-MS).

EXAMPLE 34

4,5-dianilino-monothiopthalimide

A solution of 4,5-dianilinophthalimide (0.46 g, 1.4 mmol; Example 1) in toluene (700 ml) is heated with 2,4-bis-(4-methoxyphenyl)-2,4-dithioxo- 1,3,2,4-dithiadiphosphetan (Laweson's reagent, 7 g, 17.3 mmol) during 1 h to 100° C. After evaporation, the reaction mixture is purified over silica gel with the eluent ethyl acetate/hexane 1:1. After elution of a colourless, a green and a violet band, the red-orange material being the title compound is isolated. $C_{20}H_{15}N_3OS$: molecular weight calculated 345, found 345 (FD-MS). In a further, yellow-coloured band, some dianilinophthalimide (starting material) is recovered.

EXAMPLE 35

Analogously to the mentioned processes and methods well known in the art, the following compounds can be obtained:

A) 4-(4-fluoroanilino)-5-(4-iodoanilino)-phthalimide;
B) 4-(4-fluoranilino)-5-(4-cyanoanilino)-phthalimide;
C) 4-(4-fluoroanilino)-5-(4-aminomethylanilino)-phthalimide.

What is claimed is:

1. A process for the preparation of a compound of formula I,

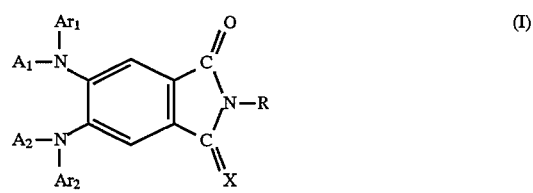

wherein $A_1$ and $A_2$ are each independently of the other hydrogen; lower alkyl; lower alkenyl; lower alkynyl; aryl; acyl which is selected from the group consisting of lower alkanoyl, halo-lower alkanoyl, aryl-lower alkanoyl, and arylcarbonyl; lower alkylsulfonyl; or arylsulfonyl;

or wherein

A₁ and A₂ together form unsubstituted or lower alkyl- or hydroxy-substituted lower alkylene;

A₁ and A₂ are each independently of the other aryl; heteroaryl selected from the group consisting of imidazolyl, triazolyl, pyridyl, pyrimidinyl, and triazinyl, each of said heteroaryls being unsubstituted or substituted, the substituents being independently selected from the group consisting of lower alkyl, hydroxy, lower alkoxy, halogen, cyano and trifluoromethyl, or unsubstituted or substituted $C_3-C_8$cycloalkyl;

the group —C(=X)— is —C(=O)—, —C(=S)—, —CH₂— or —C(=CR₁R₂)— wherein R₁ and R₂ are each independently of the other hydrogen or lower alkyl; and R is hydrogen, lower alkyl, aryl-lower alkyl, amino, hydroxy or lower alkoxy; aryl, at each occurrence being phenyl or naphthyl, and each of said aryl being unsubstituted or substituted by one or more substituents selected from the group consisting of lower alkyl, lower alkenyl, lower alkynyl, lower alkylene (linked to two adjacent carbon atoms), $C_3-C_8$cycloalkyl, phenyl-lower alkyl, phenyl, lower alkyl substituted by one or more substituents independently selected from the group consisting of lower alkyl substituted by hydroxy, lower alkoxy, phenyl-lower alkoxy, lower alkanoyloxy, halogen, amino, lower alkylamino, di-(lower alkyl) amino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and cyano; hydroxy, lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl phenylsulfinyl, lower alkylsulfonyl, phenylalkylsulfonyl, phenylsulfonyl, halogen, nitro, amino, lower alkylamino, $C_3-C_8$cycloalkylamino phenyl-lower alkylamino, phenylamino, di-(lower alkylamino), N-lower alkyl-N-phenylamino, N-lower alkyl-N-phenyl-lower alkylamino, lower alkyleneamino, lower alkyleneamino interrupted by —O—, —S— or —NR'' (wherein R'' is hydrogen, lower alkyl or lower alkanol); lower alkanoylamino, phenyl-lower alkanoylamino, phenylcarbonyl amino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N-hydroxycarbamoyl, N-phenylcarbonyl, cyano, sulfo, lower alkylsulfonyl, sulfamoyl, N-lower alkylsulfamoyl, N,N-di-lower alkylsulfamoyl and N-phenylsulfamoyl the phenyl groups in the substituents each being unsubstituted or substituted by one or more substituents selected from the group consisting of lower alkyl, lower alkoxy, hydroxy, halogen and/or by trifluoromethyl;

which process comprises:

(a) reacting a compound of formula II

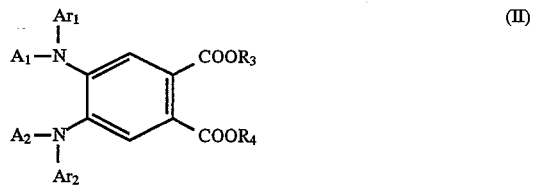

wherein Ar₁, Ar₂, A₁ and A₂ are as defined under formula I and R₃ and R₄ are each independently of the other hydrogen, aryl or lower alkyl, with a compound of formula III

wherein R is as defined under formula I or with urea, when each if R₃ and R₄ is hydrogen, or (b) reacting a compound of formula IV,

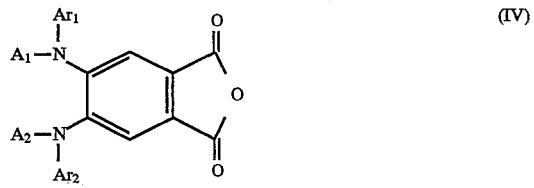

wherein Ar and A are as defined under formula I, with a compound of formula III

wherein R is as defined under formula I, or with formamide and an ensuing hydrolysis;

so as to produce a resulting compound of formula I, or a salt thereof.

2. The process according to claim 1, wherein said process further comprises a step selected from the group consisting of converting the resulting compound of formula I into a different compound of formula I, converting the salt of the resulting compound into the free compound, converting the salt of the resulting compound into a different salt, converting the resulting free compound into a salt and separating a resulting mixture of isomeric compounds of formula I into the individual isomers.

3. The process according to claim 1 for the preparation of a compound of formula I named 4,5-bis(anilino) phthalimide, which process comprises:

(a) reacting a compound of formula II, wherein each of A₁ and A₂ is hydrogen, each of Ar₁ and Ar₂ is phenyl and R₃ and R₄ are hydrogen, aryl or lower alkyl, with a compound of formula III wherein R is hydrogen, or (b) reacting a compound of formula IV, wherein each of A₁ and A₂ is hydrogen and each of Ar₁ and Ar₂ is phenyl, with a compound of formula III wherein R is hydrogen, or with formamide and an ensuing hydrolysis.

* * * * *